US008628775B2

(12) United States Patent
Lin et al.

(10) Patent No.: US 8,628,775 B2
(45) Date of Patent: Jan. 14, 2014

(54) METHODS OF REDUCING T CELL-MEDIATED IMMUNE RESPONSES WITH MULTIMERIC P-SELECTIN AND/OR E-SELECTIN COMPOUNDS

(75) Inventors: Rong-Hwa Lin, Palo Alto, CA (US); Chung Nan Chang, Foster City, CA (US)

(73) Assignee: AbGenomics Cooperatief U.A., Cm Amsterdam Zuidoost (NL)

(*) Notice: Subject to any disclaimer, the term of this patent is extended or adjusted under 35 U.S.C. 154(b) by 0 days.

(21) Appl. No.: 12/562,515

(22) Filed: Sep. 18, 2009

(65) Prior Publication Data

US 2010/0080819 A1 Apr. 1, 2010

Related U.S. Application Data

(60) Division of application No. 10/662,906, filed on Sep. 15, 2003, now abandoned, which is a continuation-in-part of application No. 10/051,497, filed on Jan. 18, 2002, now Pat. No. 7,744,888.

(60) Provisional application No. 60/310,196, filed on Aug. 3, 2001.

(51) Int. Cl.

| | |
|---|---|
| *A61K 38/17* | (2006.01) |
| *C07K 14/435* | (2006.01) |

(52) U.S. Cl.
USPC .................... 424/134.1; 424/192.1; 514/12.2; 514/20.9; 530/350; 530/387.3

(58) Field of Classification Search
None
See application file for complete search history.

(56) References Cited

U.S. PATENT DOCUMENTS

| | | | |
|---|---|---|---|
| 5,378,464 A | 1/1995 | McEver | |
| 5,593,882 A * | 1/1997 | Erbe et al. | 435/358 |
| 5,618,785 A | 4/1997 | Heavner et al. | |
| 5,709,859 A | 1/1998 | Aruffo et al. | |
| 5,710,123 A | 1/1998 | Heavner et al. | |
| 5,808,025 A | 9/1998 | Tedder et al. | |
| 5,827,817 A | 10/1998 | Larsen et al. | |
| 5,834,425 A | 11/1998 | Tedder et al. | |
| 5,840,679 A | 11/1998 | Larsen et al. | |
| 5,843,707 A | 12/1998 | Larson et al. | |
| 5,852,175 A | 12/1998 | Cummings et al. | |
| 5,972,625 A | 10/1999 | Rosen et al. | |
| 6,056,956 A | 5/2000 | Cobbold et al. | |
| 6,117,977 A | 9/2000 | Lasky et al. | |
| 6,124,267 A | 9/2000 | McEver et al. | |
| 6,210,670 B1 * | 4/2001 | Berg | 424/153.1 |
| 6,309,639 B1 | 10/2001 | Cummings et al. | |
| 6,348,581 B1 | 2/2002 | Anderson et al. | |
| 6,667,036 B2 | 12/2003 | Cummings et al. | |
| 6,884,619 B2 | 4/2005 | Hockfield et al. | |
| 7,604,800 B2 | 10/2009 | Lin et al. | |
| 7,744,888 B2 | 6/2010 | Lin et al. | |
| 8,287,871 B2 | 10/2012 | Lin et al. | |
| 8,298,540 B2 | 10/2012 | Lin et al. | |
| 8,361,472 B2 | 1/2013 | Lin et al. | |
| 2002/0031508 A1 * | 3/2002 | Wagner et al. | 424/94.63 |
| 2002/0164336 A1 | 11/2002 | Harrison et al. | |
| 2003/0049252 A1 | 3/2003 | Lin et al. | |
| 2004/0001839 A1 | 1/2004 | Levanon et al. | |
| 2004/0002450 A1 | 1/2004 | Lazarovits et al. | |
| 2004/0116333 A1 | 6/2004 | Lin et al. | |
| 2005/0152906 A1 | 7/2005 | Levanon et al. | |
| 2005/0266003 A1 | 12/2005 | Lin et al. | |
| 2006/0003940 A1 | 1/2006 | Lin et al. | |
| 2009/0191204 A1 | 7/2009 | Lin et al. | |
| 2009/0198044 A1 | 8/2009 | Lin et al. | |
| 2009/0304709 A1 | 12/2009 | Lin et al. | |
| 2011/0172397 A1 | 7/2011 | Lin et al. | |
| 2011/0178270 A1 | 7/2011 | Lin et al. | |
| 2013/0011391 A1 | 1/2013 | Bassarab et al. | |
| 2013/0011861 A1 | 1/2013 | Lin et al. | |
| 2013/0101587 A1 | 4/2013 | Lin et al. | |
| 2013/0102762 A1 | 4/2013 | Lin et al. | |

FOREIGN PATENT DOCUMENTS

| | | | |
|---|---|---|---|
| EP | 0719787 | A1 | 7/1996 |
| JP | 8-208684 | A | 8/1996 |
| JP | 09-227410 | | 9/1997 |
| WO | WO 97/06176 | | 2/1997 |
| WO | WO 97/40154 | | 10/1997 |
| WO | WO 00/25808 | | 5/2000 |
| WO | WO 02/053700 | | 7/2002 |
| WO | WO 03/013603 | | 2/2003 |
| WO | WO 2005/027831 | A2 | 3/2005 |
| WO | WO 2005/110456 | A2 | 11/2005 |
| WO | WO 2005/110475 | A2 | 11/2005 |
| WO | WO 2012/174001 | A1 | 12/2012 |

OTHER PUBLICATIONS

GENBANK Submission; NIH/NCBI, Accession No. AAA40008; Weller et al.; Oct. 7, 2005.

Chamow et al., Immunoadhesins: principles and applications. Trends Biotechnol. Feb. 1996;14(2):52-60.

Coito et al., Selectin-mediated interactions regulate cytokine networks and macrophage heme oxygenase-1 induction in cardiac allograft recipients. Lab Invest. Jan. 2002;82(1):61-70.

Dietsch et al., Bispecific receptor globulins, novel tools for the study of cellular interactions. Preparation and characterization of an E-selectin/P-selectin bispecific receptor globulin. J Immunol Methods. Jun. 4, 1993;162(1):123-32.

Griffiths et al., Psoriasis, T cells and autoimmunity. J R Soc Med. Jun. 1996;89(6):315-9. Review.

(Continued)

*Primary Examiner* — Phillip Gambel

(74) *Attorney, Agent, or Firm* — Wolf, Greenfield & Sacks, P.C.

(57) ABSTRACT

Multimeric compounds that bind to P-Selectin Glycoprotein 1 (PSGL-1) on the surface of T cells or natural killer (NK) cells can be used to induce T cell or NK cell depletion and/or to induce T cell or NK cell apoptosis. The multimeric compounds and methods of the invention can be used to control unwanted T cell- or NK cell-mediated immune responses in conditions such as inflammatory diseases, autoimmune diseases, transplant rejection, and allergic diseases.

20 Claims, 12 Drawing Sheets

(56) References Cited

OTHER PUBLICATIONS

Ho et al., The history and future of T-cell depletion as graft-versus-host disease prophylaxis for allogeneic hematopoietic stem cell transplantation. Blood. Dec. 1, 2001;98(12):3192-204.

Huang et al., A novel apoptosis-inducing anti-PSGL-1 antibody for T cell-mediated diseases. Eur J Immunol. Jul. 2005;35(7):2239-49.

Konstantinow et al., Treatment of cutaneous T-Cell lymphoma with extracorporeal photochemotherapy. J Eur Acad Dermatol Venereol. 1997;9:111-117.

Lassman, The pathology of multiple sclerosis and its evolution. Philos Trans R Soc Lond B Biol Sci. Oct. 29, 1999;354(1390):1635-40.

Olsen et al., In vivo T cell depletion in rheumatoid arthritis is associated with increased in vitro IgM-rheumatoid factor synthesis. Clin Immunol Immunopathol. May 1993;67(2):124-9.

Stirling et al., Future treatments of allergic diseases and asthma. Br Med Bull. 2000;56(4):1037-53.

Menta et al., Affinity and kinetic analysis of P-selectin binding to P-selectin glycoprotein ligand-1. J Biol Chem. 1998;273(49):32506-13.

Battistini et al., CD8+ T cells from 1-37 patients with acute multiple sclerosis display selective increase of adhesiveness in brain venules: A critical role for P-selectin glycoprotein ligand-1. *Blood* vol. 101, No. 12, 4775-4782; Jun. 15, 2003.

Beckwith et al. The protein product of the proto-oncogene c-cbl forms a complex with phosphatidylinositol 3-kinase p85 and CD19 in anti-IgM stimulated human B-lymphoma cells, *Blood* 88(9): 3502-3507, 1996.

Besnault et al., B cell receptor cross-linking triggers a caspase-8-dependent apoptotic pathway that is independent of the death effector domain of fas-associated death domain protein, *J. Immunol.* 167:733-740; 2001.

Borges et al., P-selectin glycoprotein ligand-1 (PSGL-1) on T helper 1 but not on T helper 2 cells binds to P-selectin and supports migration into inflamed skin, *J. Exp. Med.* 185(3): 573-578; Feb. 3, 1997.

Borges et al., The binding of T cell-expressed P-selectin glycoprotein ligand-1 to E- and P-selectin is differentially regulated; *J. Biol. Chem.* 272(45): 28786-28792; Nov. 7, 1997.

Chen SC et al., Cross-linking of P-selectin glycoprotein ligand-1 induces death of activated T cells. *Blood* Nov. 15, 2004; 104(10); 3233-42; Epub Jun. 15, 2004.

Damle NK et al., GMP-140 (P-selectin/CD62) binds to chronically stimulated but not resting CD4+ T lymphocytes and regulates their production of proinflammatory cytokines. *Eur J Immunol.* Jan. 1, 1992; 22(7): 1789-1793.

Diacovo et al., Interactions of human alpha/beta and gamma/delta T lymphocytes subsets in shear flow with E-selectin and P-selectin, J. Exp. Med. vol. 183, 1193-1203; Mar. 1996.

Dimitroff et al., Glycosylation-dependent inhibition of cutaneous lymphocyte-associated antigen expression: Implications in modulating lymphocyte migration to skin. *Blood*, vol. 101, No. 2, 602-610; Jan. 15, 2003.

European Search Report from corresponding European Application No. 04783669 dated May 19, 2009.

Evangelista et al., Platelet/polymorphonuclear leukocyte interaction: P-selectin triggers protein-tyrosine phosphorylation-dependent CD11b/CD18 adhesion: Role of PSGL-1 as a signaling molecule, *Blood* 93(3): 876-885; Feb. 1, 1999.

Faraday et al., Leukocytes can enhance platelet-medicated aggregation and thromboxane release via interaction of P-selectin glycoprotein ligand with P-selectin. *Anesthesiology* 94(1): 145-151; Jan. 2001.

Frenette et al., P-selectin glycoprotein ligand 1 (PSGL-1) is expressed on platelets and can mediate platelet-endothelial interactions in vivo. *J. Exp. Med.* 191(8): 1413-1422; Apr. 17, 2000.

Fuhlbrigge et al., Cutaneous lymphocyte antigen is a specialized form of PSGL-1 expressed on skin-homing T cells. *Nature* 389-978-981; Oct. 1997.

Herron MJ et al., Intracellular parasitism by the human granulocytic ehrlichiosis bacterium through the P-selectin ligand, PSGL-1. *Science* Jun. 2, 2000: 288(5471); 1653-6.

Hirata et al., P-selectin glycoprotein ligand 1 (PSGL-1) is a physiological ligand for E-selectin in mediating T helper 1 lymphocyte migration. *J. Exp. Med.* 192(11): 1669-1675; Dec. 4, 2000.

Hirose et al., A functional epitope on P-selectin that supports binding of P-selectin to P-selectin glycoprotein ligand-1 but not to sialyl Lewis X oligosaccharides. *Internatl. Immunol.* 10(5): 639-649; Jan. 26, 1998.

Igarashi et al., Telomerase activity is induced in human peripheral B lymphocytes by the stimulation to antigen receptor. Blood 89(4): 1299-1307; 1997.

Kaytes et al., P-selectin mediates adhesion of the human melanoma cell line NKI-4: Identification of glycoprotein ligands. *Biochemistry* vol. 37, No. 29, 10514-10521; Jul. 21, 1998.

Kieffer et al., Neutrophilis, monocytes, and dendritic cells express the same specialized form of PSGL-1 as do skin-homing memory T cells: Cutaneous lymphocyte antigen. *Biochem. Biophys. Res. Comm.* vol. 285, No. 3, 577-587; Jul. 20, 2001.

Kunzendorf U et al., T cells bind to the endothelial adhesion molecule GMP-140 (P-selectin). *Transplantation.* Nov. 1993; 56(5); 1213-1217.

Laszik et al., P-selectin glycoprotein ligand-1 is broadly expressed in cells of myeloid, lymphoid, and dendritic lineage and in some nonhematopoietic cells. *Blood* 88(8): 3010-3021; Oct. 15, 1996.

Levesque et al., PSGL-1 mediated adhesion of human hematopoietic progenitors to P-selectin results in suppression of hematopoiesis. *Immunity* 11:369-378; Sep. 1999.

Li et al., Visualization of P-selectin glycoprotein ligand-1 as a highly extended molecule and mapping of protein epitopes for monoclonal antibodies. *J. Biol. Chem.* 271(11): 6342-6348; 1996.

Moore et al., P-selectin glycoprotein ligand-1 mediates rolling of human neutrophils on P-selectin. *J. Cell Biol.* 128(4): 661-671; 1995.

Nizet Y et al., The experimental (in vitro) and clinical (in vivo) immunosuppressive effects of a rat IgG2b anti-human CD2 mAb, LO-CD2a/BTI-322, *Transplantation* 69 (7): 1420-1428; 2000.

Sako D. et al., Expression cloning of a functional glycoprotein ligand for P-selectin. *Cell* Dec. 17, 1993; 75(6): 1179-86.

Shan et al., Apoptosis of malignant human B cells by ligation of CD20 with monoclonal antibodies. *Blood* 91(5): 1644-1652; 1998.

Snapp et al., A novel P-selectin glycoprotein ligand-1 monoclonal antibody recognizes an epitope within the tyrosine sulfate motif of human PSGL-1 and blocks recognition of both P- and L-selectin. *Blood* 91(1): 154-164; Jan. 1, 1998.

Stockmeyer et al., Polymorphonuclear granulocytes induce antibody-dependent apoptosis in human breast cancer cells. *J. Immunol.* 171:5124-5129; 2003.

Trembleau et al., Pancreas-infiltrating Th1 cells and diabetes develop in IL-12 deficient nonobese diabetic mice. *J. Immunol.* 164:2960-2968; 1999.

Tsukamoto K et al., Administration of monoclonal antibodies against vascular cell adhesion molecule-1/very late antigen-4 abrogates predisposing autoimmune diabetes in NOD mice; *Cell Immunol.* 165:193-201; 1995.

U.S.P.T.O. Office Action dated Jul. 31, 2006 in U.S. Appl. No. 10/051,497.

U.S.P.T.O. Office Action dated Apr. 19, 2007 in U.S. Appl. No. 10/051,497.

Vachino G. et al., P-selectin glycoprotein ligand-1 is the major counter-receptor for P-selectin on stimulated T cells and is widely distributed in non-functional form on many lymphocytic cells. *J. Biol. Chem.* Sep. 15, 1995; 270(37): 21966-74.

Veldman G.M. et al., Genomic organization and chromosomal localization of the gene encoding human P-selectin glycoprotein ligand. *J. Biol. Chem.* Jul. 7, 1995; 270(27): 16470-5.

Wing et al., Mechanism of first-dose cytokine-release syndrome by CAMPATH 1-H: Involvement of CD16 (FcγRIII) and CD11a/CD18 (LFA-1) on NK cells. *J. Clin. Invest.* 98(12): 2819-2826; 1996.

(56) References Cited

OTHER PUBLICATIONS

Woltmann et al., Interleukin-13 induces PSGL-1/P-selectin-dependent adhesion of eosinophils, but not neutrophils, to human umbilical vein endothelial cells under flow. *Blood* vol. 95, No. 10, 3146-3152; May 15, 2000.

Wu et al., Role of P-selectin and anti-P-selectin monoclonal antibody in apoptosis during hepatic/renal ischemia reperfusion injury. *World J. Gastroentero* 6(2):244-247; 2000.

Yago et al., IL-12 promotes the adhesion of NK cells to endothelial selectins under flow conditions. *J Immunol.* 161:1140-1145; 1998.

Yang et al., Targeted gene disruption demonstrates that p-selectin glycoprotein ligand 1 (PSGL-1) is required for P-selectin-mediated but not E-selectin-mediated neutrophil rolling and migration. *J. Exp. Med.* 190(12): 1769-1782; Dec. 20, 1999.

\* cited by examiner

Ab IP: Antibody used for immunoprecipitation
TA-B4: TA-B4 monoclonal antibody
HNS: Hamster normal serum

CD4 T

CD8 T

CD19+

Pan-NK+

TAB4

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Ile Glu Gly Arg Met Asp
1               5

<210> SEQ ID NO 2
<211> LENGTH: 6
<212> TYPE: PRT
<213> ORGANISM: Artificial sequence
<220> FEATURE:
<223> OTHER INFORMATION: synthetic peptide

<400> SEQUENCE: 2

His His His His His His
1               5
```

METHODS OF REDUCING T CELL-MEDIATED IMMUNE RESPONSES WITH MULTIMERIC P-SELECTIN AND/OR E-SELECTIN COMPOUNDS

RELATED APPLICATIONS

This application is a divisional of U.S. application Ser. No. 10/662,906, filed Sep. 15, 2003, now abandoned, which is a continuation-in-part of U.S. application Ser. No. 10/051,497, filed Jan. 18, 2002, now U.S. Pat. No. 7,744,888, which claims priority of U.S. Application No. 60/310,196, filed Aug. 3, 2001. The prior applications are incorporated herein by reference in their entirety.

FIELD OF THE INVENTION

The invention relates to compositions and methods for controlling immune responses.

BACKGROUND OF THE INVENTION

The control of unwanted immune responses is a critical issue in the treatment of diseases such as inflammatory diseases, autoimmune diseases, transplant rejection, allergic diseases and T cell-derived cancers. The activity of overly aggressive T cells can be controlled by immunosuppression or by the induction of immunological tolerance. Tolerance is defined as a state where the immune system is made unresponsive to an antigen, whereas immunosuppression, which decreases the immune response to antigens, usually requires the continued use of medication. In organ transplantation, T cells play an essential role in the immune response to alloantigens. Current immunosuppressive regimes commonly involve the use of corticosteroid, cyclosporin or rapamycin, which block the transcription of IL-2, a key growth factor for T cells, or inhibit IL-2 dependent proliferation. However, a number of monoclonal antibodies which either act as T cell-depleting agents (e.g. CD3, CD4, CD8), or as inhibitors of the cytokine signaling or the co-stimulatory pathways of T cells (e.g. CD25, B7-1, B7-2, CD152, CTLA4) have demonstrated effectiveness in reducing the incidence of rejection with limited side effects or toxicity. Some of these agents have been shown to have some degree of success in treating autoimmune disease and in prolonging graft survival.

Apoptosis is widely believed to be of vital importance for maintaining the proper function of the immune system and a major mechanism to remove unwanted cells (Kabelitz et al. Immunol. Today 14:338-340 (1993); Raff, Nature:356:397-399 (1992)). Various signals originating from either inside or outside a cell influence the life and death of the cell. Antibodies against T cell surface molecules such as Fas (or CD95, MW=43 kD), TNFR2 (MW=75 kD), CD2 (MW=45 kD) and CTLA-4 (MW=33 kd)) induce the apoptosis of T cells (Osborne, Curr. Opin. Immunol. 8:245-248 (1996); Lin et al. J. Immunol. 158:598-603 (1997); Zhang et al. Nature:377:348-350 (1995); Lai et al. Eur. J. Immunol. 25:3243-3248 (1995); Mollereau et al. J. Immunol. 156:3184-3190 (1996); Gribben et al. Proc. Natl. Acad. Sci. USA 92:811-815 (1995)). Attempts to use Fas and TNFR2 molecules to control unwanted T cells have been hampered by the fact that these two molecules are expressed not only on immune cells, but also on several other important organ systems like liver. This expression pattern potentially limits the therapeutic application of these two antibodies (Ogasawara et al. Nature 364:806-809 (1993); Pfeffer et al. Cell:73:457-467 (1993); Engelmann et al. J. Biological Chemistry 265:14497-14504 (1990)).

Selectins, integrins and immunoglobulin (Ig) superfamily members are three major classes of adhesion molecules that are important to the interaction of leukocytes and platelets either with themselves or with the extracellular matrix and vascular endothelium (Springer, Nature 346:425 (1990); Osborn, Cell 62:3 (1990); Hynes, Cell 69:11 (1992)). An adhesion molecule on one cell type often binds to another adhesion molecule expressed on a different cell type, forming a ligand-receptor pair.

The selectin family consists of P-selectin (also known as CD62, CD62P, GMP140, and PADGEM), E-selectin (also known as ELAM-1 and CD62E), and L-selectin (also known as LECAM-1, Mel-14, LAM-1, and CD62L). The selectins are highly homologous, composed of a 120 amino acid N-terminal lectin domain, an EGF-like domain, a variable number of multiple short consensus repeat (SCR) domains homologous to those found in complement regulatory proteins, followed by a transmembrane domain and short cytoplasmic tail (Siegelman et al., Science 243:1165-1172 (1989); Lasky et al., Cell 56:1045-1055 (1989); Tedder et al., J. Exp. Med. 170:123-133 (1989); Johnson et al., Cell 56:1033-1044 (1989); Bevilacqua et al., Proc. Natl. Acad. Sci. USA 84:9238-9242 (1987), Bevilacqua et al., Science 243:1160-1165 (1989), Bevilacqua et al., J. Clin. Invest. 91:379-387 (1993), Camerini et al., Nature 280:496-498 (1989)). The selectins have overlapping but distinct specificities for cell surface receptors (Bevilacqua et al., J. Clin. Invest. 91:379-387 (1993); Feize, Current Opinion in Struct. Biol. 3:701-710 (1993); Berg et al., Biochem. Biophys. Res. Comm. 184:1048-1055 (1992); Foxall et al., J. Cell Biol. 117:895-902 (1992); Larsen et al., J. Biol. Chem. 267:11104-11110 (1992); Polley et al., Proc. Natl. Acad. Sci. USA 88:6224-6228 (1991)).

P-selectin, E-selectin, and L-selectin mediate the first leukocyte-endothelial cell and platelet-leukocyte adhesive interactions during inflammation (Bevilacqua et al., 1993, supra). All three selectins have been demonstrated to participate in an initial "rolling" interaction of leukocytes with activated endothelium (von Andrian et al., Proc. Natl. Acad. Sci. USA 88:7538-7542 (1991); Ley et al., Blood 77:2553-2555 (1991); Abassi et al., J. Clin. Invest. 92:2719-2730 (1993); Dore et al., Blood 82:1308-1316 (1993); Jones et al., Biophys. J. 65:1560-1569 (1993); Mayadas et al., Cell 74:541-554 (1993)). P-selectin, expressed on activated platelets and endothelial cells, binds to cell surface proteins on most leukocytes (McEver et al., J. Biol. Chem. 250:9799-9804 (1984); Hsu-Lin et al., J. Biol. Chem. 264:8121-9126 (1984)). E-selectin, expressed on cytokine-activated endothelial cells (e.g., after TNF-alpha or IL-1 stimulation for 6-8 hours) binds to cell surface proteins on most leukocytes (McEver et al., J. Clin. Invest. 100:485-492 (1997); Bevilacqua et al., 1987, supra; Bevilacqua et al., 1989, supra). L-selectin, expressed on most leukocytes, binds to cell surface proteins on some endothelial cells and on other leukocytes (Gallatin et al., Nature 304:30-34 (1983); Berg et al., Immunol. Rev. 108:5-18 (1989); Berg et al., J. Cell. Biol. 114:343-349 (1991), Hallman et al., Biochem. Biophys. Res. Comm. 174:236-243 (1991); Smith et al., J. Clin. Invest. 87:609-618 (1991); Spertini et al., J. Immunol. 147:2565-2573 (1991)). All three selectins have been shown to bind to a cell surface protein, PSGL-1, whose expression is largely limited to leukocytes, and in particular T cells and NK cells. Posttranslational modifications of PSGL-1 are required for binding to P-selectin, E-selectin, and L-selectin (McEver et al., J. Clin. Invest., 1997, supra).

SUMMARY OF THE INVENTION

The invention is based on the discovery that T cells can be depleted and/or induced to undergo apoptosis by the engagement of the T cell surface antigen P-Selectin Glycoprotein Ligand-1 (PSGL-1). T cell depletion can be particularly useful for the treatment of conditions associated with an excessive or unwanted T cell-mediated immune response or excessive or unwanted T cell proliferation. For example, the depletion of T cells can cause the reduction or elimination of undesirable T cell activity or proliferation associated with inflammatory diseases, autoimmune diseases, transplant rejection, allergic diseases, and/or T cell-derived cancers. The invention encompasses methods of using modulators of PSGL-1 function to prevent or reduce a T cell-mediated immune response as well as methods of screening for modulators of PSGL-1 function.

In one aspect, the invention features a method of preventing or reducing a T cell-mediated immune response in an individual. The method includes the following steps: selecting an individual diagnosed as having or as being at risk of acquiring a condition characterized by an excessive or unwanted T cell-mediated immune response; and administering to the individual a compound that binds to PSGL-1 on the surface of a T cell, wherein the binding of the compound to PSGL-1 on the surface of the T cell induces a signal transduction pathway that results in the death of the T cell, thereby preventing or reducing a T cell-mediated immune response in the individual.

The compound used in such a method can include an antibody or antigen binding fragment thereof that specifically binds to PSGL-1. In one example, the compound is a monoclonal antibody that specifically binds to PSGL-1. In one embodiment, the method includes an additional step of administering an agent that binds to the monoclonal antibody and induces the cross-linking of a plurality of PSGL-1 antigens on the surface of the T cell.

In some embodiments, the method includes inducing the cross-linking of a plurality of PSGL-1 antigens on the surface of the T cell, wherein the cross-linking induces the signal transduction pathway that results in the death of the T cell.

In some embodiments, the method includes the following steps: (i) selecting an individual diagnosed as having or as being at risk of acquiring a condition characterized by an excessive or unwanted T cell-mediated immune response; and (ii) administering to the individual a multimeric compound that binds to at least two PSGL-1 proteins on the surface of a T cell, wherein the multimeric compound contains two polypeptide chains, each of the polypeptide chains including (a) a binding domain that binds to PSGL-1, and (b) a heterologous amino acid sequence, wherein the polypeptide chains are linked via the heterologous amino acid sequence to form the multimeric compound, and wherein the binding of the multimeric compound to the at least two PSGL-1 proteins on the surface of the T cell induces a signal transduction pathway that results in the death of the T cell, thereby preventing or reducing a T cell-mediated immune response in the individual.

The multimeric compound can be a homo-multimeric compound or a hetero-multimeric compound. The binding domain can optionally contain a P-Selectin extracellular domain or a PSGL-1-binding fragment thereof, an E-Selectin extracellular domain or a PSGL-1-binding fragment thereof, an L-Selectin extracellular domain or a PSGL-1-binding fragment thereof, an anti-PSGL-1 antibody or a PSGL-1-binding fragment thereof, a PSGL-1 binding polypeptide selected from a phage display library, or a combination of any of the above.

In certain embodiments, the multimeric compound does not include an anti-PSGL-1 antibody or an antibody fragment that binds to PSGL-1.

The heterologous amino acid sequence can optionally contain a cell surface receptor binding region, e.g., an immunoglobulin heavy chain constant region. In some embodiments, the polypeptide chains are covalently linked, e.g., disulfide linked, via the heterologous amino acid sequence to form the multimeric compound.

In certain embodiments, the method can include an additional step of administering to the individual an agent that binds to the multimeric compound via the heterologous amino acid sequence and induces cross-linking of a plurality of PSGL-1 antigens on the surface of the T cell.

In some embodiments, a method described herein includes a step of selecting an individual diagnosed as having an autoimmune disease. In another example, the method includes a step of selecting an individual diagnosed as having an inflammatory disease. In another example, the method includes a step of selecting an individual that has received or is expected to receive an allogeneic or xenogeneic transplant. In another example, the method includes a step of selecting an individual diagnosed as having an allergic disease. In another example, the method includes a step of selecting an individual diagnosed as having a T cell cancer.

In some embodiments, the T cell is an activated T cell. In one example, the T cell is a $CD4^+$ T cell. In another example, the T cell is a $CD8^+$ T cell.

In some embodiments, the method includes a step of detecting the number of T cells in a first biological sample taken from the individual before the administration of the compound (e.g., a multimeric compound) and comparing the results with the number of T cells in a second biological sample taken from the individual after the administration of the compound (e.g., a multimeric compound).

In some embodiments, the method includes a step of detecting a biological activity of T cells in a first biological sample taken from the individual before the administration of the compound (e.g., a multimeric compound) and comparing the results with the biological activity of T cells in a second biological sample taken from the individual after the administration of the compound (e.g., a multimeric compound).

In some embodiments, the administration results in the depletion of at least 10% of activated T cells in the individual. In some embodiments, the administration results in the depletion of at least 10%, 20%, 30%, 40%, 50%, or more of the activated T cells in the individual.

In some embodiments, the antibody or antigen binding fragment thereof or the multimeric compound induces the death of at least 10% of activated T cells in the individual after exposure to the antibody or antigen binding fragment thereof or the multimeric compound. In some embodiments, the administration induces the death of at least 10%, 20%, 30%, 40%, 50%, or more of the activated T cells in the individual. Cell death can be measured at any time, e.g., one, two, three, four, five, six, seven, or more days after exposure to the antibody or antigen binding fragment thereof or the multimeric compound.

In another aspect, the invention features a method of inducing the death of a T cell or a natural killer (NK) cell. The method includes the steps of: providing a T cell or NK cell expressing PSGL-1 on its cell surface; and contacting the T cell or NK cell with a compound that binds to PSGL-1 on the surface of the T cell or NK cell, wherein the binding of the compound to PSGL-1 on the surface of the T cell or NK cell induces a signal transduction pathway that results in the death of the T cell or NK cell.

The compound used in such a method can include an antibody or antigen binding fragment thereof that specifically binds to PSGL-1. In one example, the compound is a monoclonal antibody that specifically binds to PSGL-1. In one embodiment, the method includes a step of contacting the monoclonal antibody with an agent that binds to the monoclonal antibody and induces the cross-linking of a plurality of PSGL-1 antigens on the surface of the T cell or NK cell.

In one embodiment, the method includes the following steps: (i) providing a T cell or NK cell expressing PSGL-1 on its cell surface; and (ii) contacting the T cell or NK cell with a multimeric compound that binds to at least two PSGL-1 proteins on the surface of the T cell or NK cell, wherein the multimeric compound contains two polypeptide chains, each of the polypeptide chains including (a) a binding domain that binds to PSGL-1, and (b) a heterologous amino acid sequence, wherein the polypeptide chains are linked via the heterologous amino acid sequence to form the multimeric compound, wherein the binding of the multimeric compound to the at least two PSGL-1 proteins on the surface of the T cell or NK cell induces a signal transduction pathway that results in the death of the T cell or NK cell.

The multimeric compound can be a homo-multimeric compound or a hetero-multimeric compound. The binding domain can optionally contain a P-Selectin extracellular domain or a PSGL-1-binding fragment thereof, an E-Selectin extracellular domain or a PSGL-1-binding fragment thereof, an L-Selectin extracellular domain or a PSGL-1-binding fragment thereof, an anti-PSGL-1 antibody or a PSGL-1-binding fragment thereof, a peptide selected from a phage display library, or a combination of any of the above.

The heterologous amino acid sequence can optionally contain a cell surface receptor binding region, e.g., an immunoglobulin heavy chain constant region. In some embodiments, the polypeptide chains are covalently linked, e.g., disulfide linked, via the heterologous amino acid sequence to form the multimeric compound.

In some embodiments, the method includes an additional step of contacting the multimeric compound with an agent that binds to the multimeric compound via the heterologous amino acid sequence and induces cross-linking of a plurality of PSGL-1 antigens on the surface of the T cell.

In some embodiments, the method includes a step of inducing the cross-linking of a plurality of PSGL-1 antigens on the surface of the T cell or NK cell, wherein the cross-linking induces the signal transduction pathway that results in the death of the T cell or NK cell.

In some embodiments of methods described herein, the T cell is an activated T cell. In one example, the T cell is a CD4$^+$ T cell. In another example, the T cell is a CD8$^+$ T cell.

In some embodiments of methods described herein, the method includes a step of assessing the viability of the T cell or NK cell after the contacting with the compound (e.g., a multimeric compound).

In some embodiments of methods described herein, the method includes a step of assessing a biological activity of the T cell or NK cell after the contacting with the compound (e.g., a multimeric compound).

In some embodiments, the method includes inducing the death of an activated T cell.

In another aspect, the invention features a method of screening for a modulator of PSGL-1 function. The method includes the steps of: providing a cell expressing PSGL-1 on the surface of the cell; contacting the cell with a test substance; and measuring the viability of the cell after contacting the cell with the test substance to thereby determine if the test substance is a modulator of PSGL-1 function.

In one embodiment, the method includes the step of detecting the death of the cell induced by the test substance to thereby determine that the test substance is a modulator of PSGL-1 function.

In one embodiment, the test substance is an antibody or antigen binding fragment thereof that specifically binds to PSGL-1. In one example, the test substance is a monoclonal antibody that specifically binds to PSGL-1. In one embodiment, the method includes the step of contacting the monoclonal antibody with an agent that binds to the monoclonal antibody and induces the cross-linking of a plurality of PSGL-1 antigens on the surface of the cell.

In one embodiment, the method includes the step of inducing the cross-linking of a plurality of PSGL-1 antigens on the surface of the cell, wherein the cross-linking induces the signal transduction pathway that results in the death of the cell.

In one embodiment, the T cell is an activated T cell. In one example, the T cell is a CD4$^+$ T cell. In another example, the T cell is a CD8$^+$ T cell.

In one embodiment, the method includes the step of manufacturing bulk quantities of the test substance and formulating the test substance in a pharmaceutically acceptable carrier.

In another aspect, the invention features a kit containing: a compound that binds to PSGL-1 on the surface of a T cell, wherein the binding of the compound to PSGL-1 on the surface of the T cell induces a signal transduction pathway that results in the death of the T cell; and instructions for use of the compound to treat a condition associated with an excessive or unwanted T cell mediated immune response or excessive or unwanted T cell proliferation such as inflammation, autoimmunity, transplant rejection, an allergic condition, or a T cell cancer.

In one embodiment, the kit contains: (i) a multimeric compound that binds to at least two PSGL-1 proteins on the surface of a T cell, wherein the multimeric compound contains two polypeptide chains, each of the polypeptide chains including (a) a binding domain that binds to PSGL-1, and (b) a heterologous amino acid sequence, wherein the polypeptide chains are linked via the heterologous amino acid sequence to form the multimeric compound, wherein the binding of the multimeric compound to the at least two PSGL-1 proteins on the surface of the T cell induces a signal transduction pathway that results in the death of the T cell; and (ii) instructions for use of the compound to treat a condition associated with an excessive or unwanted T cell mediated immune response or excessive or unwanted T cell proliferation such as inflammation, autoimmunity, transplant rejection, an allergic condition, or a T cell cancer.

An advantage of the invention is that it can induce the depletion of T cells and/or the induction of apoptosis in T cells without causing an associated unwanted or harmful immune response. For example, in some embodiments the administration to an individual of an anti-PSGL-1 antibody or a multimeric compound described herein does not result in an unwanted elevation in the levels of inflammatory cytokines such as IL-2 or TNF-alpha.

Another advantage of the invention is that it causes the depletion of T cells by the use of agonistic compositions that induce apoptosis of T cells. Accordingly, the invention provides for active immunosuppressive methods rather than passive immunosuppression that results from using antagonistic compositions (e.g., antagonistic anti-PSGL-1 antibodies or antagonistic soluble selectin fragments) that act by binding immune receptors and preventing immune activation mediated by such receptors.

Another advantage of the invention is that it allows for the targeting of a cell surface protein, PSGL-1, whose expression is largely limited to leukocytes, and in particular T cells and NK cells. Therefore, the compounds described herein generally do not induce significant levels of apoptosis of other cell types such as liver cells. The targeting of T cells and NK cells (an important CD3⁻ cell type involved in transplantation rejection) for selective depletion, without significantly inducing life-threatening systemic cytokine responses and damaging other organ systems, is a desired characteristic of an immunosuppressive agent.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of a conflict in terminology, the present specification will control. In addition, the described materials and methods are illustrative only and are not intended to be limiting.

Other features and advantages of the invention will be apparent from the following detailed description and the claims.

DETAILED DESCRIPTION

Figure 1:
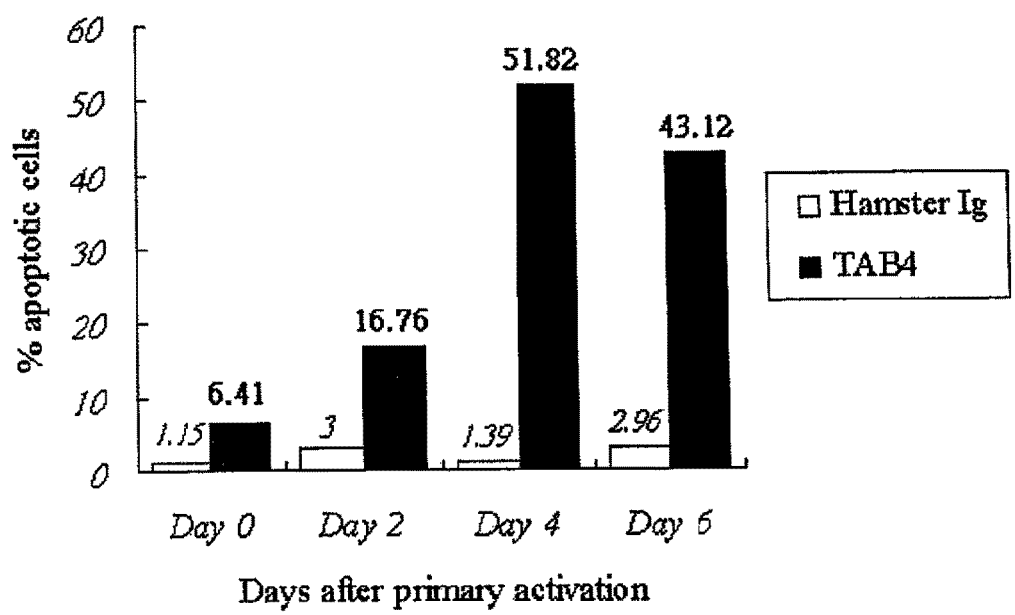
FIG. 1 depicts the results of a time-course experiment that investigated when activated T cells acquire sensitivity to TAB4 (an anti-PSGL-1 monoclonal antibody)-mediated apoptotic signals.

The invention is directed to methods of modulating T cell activity by modulating the function of PSGL-1 molecules residing on the surface of a T cell. Engagement of PSGL-1 with agonist compositions described herein can cause the depletion of T cells and/or induce T cells to undergo apoptosis. These agonist compositions are therefore useful as therapeutic agents for controlling immune-related conditions such as inflammatory diseases, autoimmune diseases, transplant rejection, allergic diseases, and/or T cell-derived cancers. The agonist compositions are also useful in causing the depletion of T cells from any biological sample where the presence or activity of T cells is not desired.

PSGL-1 Protein

PSGL-1 is a cell surface adhesion molecule that is expressed on neutrophils, T and B-lymphocytes, NK cells, monocytes, dendritic cells, and primitive human CD34 hematopoietic progenitor cells. Through its ability to interact with selectins, PSGL-1 mediates the rolling of leukocytes on the endothelium and the extravasation of leukocytes into inflamed tissues. PSGL-1-mediated binding of T cells to E- and P-selectin, or migration, is differentially regulated. For instance, the appearance of CLA (cutaneous lymphocyte antigen) epitope is thought to be induced on T cells undergoing naive to memory transition. Only activated helper 1 but not helper 2 T cells express functional PSGL-1 and are capable of migration into the inflamed area of the skin.

PSGL-1 is a sialomucin that must be specifically sialylated, fucosylated, and sulfated to bind P-selectin. The PSGL-1 molecule exists in isoforms characterized by different degree of glycosylation and sulfation sites at their N-termini. Resting peripheral blood T and B cells, lymphoid cell lines, and in vitro activated peripheral blood T cells express similar level of PGSL-1. Yet, only activated T cells display a functional form of PSGL-1 and bind avidly to P-selectin. Such activation-dependent binding activity appears to be a result of differential post-translational modification, as suggested by elevated levels of alpha (1,3) fucosyltransferases activities in activated T cells. PSGL-1 isoforms also show differential affinity to L-selectin and E-selectin. For instance, human T cells exhibiting the CLA-positive isoform can tether and roll on both E- and P-selectin, while T cells expressing PSGL-1 without the CLA epitope only bind to P-selectin. Furthermore, binding of PSGL-1 to P-selectin is contingent upon the presence of the terminal decapeptide that contains three tyrosine residues for sulfation and one threonine residue for glycosylation.

A PSGL-1 protein can be prepared by recombinant methods and/or by isolating a native PSGL-1 protein from biological material. A recombinant PSGL-1 protein can be produced in prokaryotic or eukaryotic cells, either in vitro or in vivo. Nucleic acids encoding PSGL-1 can be used for recombinant production of the protein (see, e.g., GenBank™ Accession NM_003006 for an example of a nucleic acid encoding a PSGL-1 polypeptide). Antibodies directed to PSGL-1 are also well known and can be used for purification of the antigen (see, e.g., Herron et al. (2000) Science June 2; 288(5471):

1653-56; WO 00/25808) and/or used in methods described herein. PSGL-1 is further described in references including but not limited to Sako et al. (1993) Cell 75:1179; Vachino et al. (1995) J. Biol. Chem. 270:21966; and Veldman et al. (1995) J. Biol. Chem. 270:16470.

For recombinant production of PSGL-1, the simultaneous expression of both PSGL-1 and its modifying alpha-(1,3) fucosyltransferase, Fuc-TVII, may be required for the functional expression of PSGL-1. In addition or alternatively, recombinant production of PSGL-1 may be accompanied by co-transfection with a nucleic acid encoding PACE for removing the propeptide and/or or a nucleic acid encoding tyrosine sulfotransferase.

An anti-PSGL-1 antibody can be used to isolate and purify a PSGL-1 antigen from biological material. Any cell type expressing a PSGL-1 protein, e.g., T cells derived from an individual or a T cell line, can be used as a source of the protein. Once purified, the protein can be used in a variety of methods as described herein. For example, the purified PSGL-1 protein can be used in an in vitro screen of modulators of PSGL-1 function on T cells or as an immunogen to prepare antibodies directed against the protein.

Anti-PSGL-1 Antibodies

PSGL-1 polypeptides (or immunogenic fragments or analogs thereof) can be used to generate antibodies useful in the methods of the invention. As described above, PSGL-1 polypeptides or peptide fragments thereof can be produced by recombinant techniques or synthesized using solid phase synthesis methods. The recombinant PSGL-1 polypeptides or a peptide fragment thereof can be used as an immunogen to produce anti-PSGL-1 antibodies. In addition, an anti-PSGL-1 antibody, such as the TAB4 monoclonal antibody, can be used to purify a PSGL-1 polypeptide, e.g., a PSGL-1 polypeptide in its natural conformation, which can then be used as an immunogen to produce additional anti-PSGL-1 antibodies.

An antibody of the invention can be a monoclonal, polyclonal, or engineered antibody that specifically binds to a PSGL-1 polypeptide. An antibody that "specifically binds" to a particular antigen, e.g., a PSGL-1 polypeptide, will not substantially recognize or bind to other molecules in a sample. Thus, the invention also features methods for identifying a test compound (e.g., an antibody) that binds to a polypeptide of the invention by contacting the polypeptide with a test compound and determining whether the polypeptide binds to the test compound (e.g., by direct detection of the binding, detection of a competitor molecule which disrupts binding of the test compound to the polypeptide, and/or detection of binding using an assay for apoptosis-inducing activity).

In general, PSGL-1 polypeptides can be coupled to a carrier protein, such as KLH, mixed with an adjuvant, and injected into a host mammal. Antibodies produced in that animal can then be purified by peptide antigen affinity chromatography.

In particular, various host animals can be immunized by injection with a PSGL-1 polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the PSGL-1 polypeptides described above and standard hybridoma technology (see, for example, Kohler et al., Nature 256:495 (1975); Kohler et al., Eur J Immunol 6:511 (1976); Kohler et al., Eur J Immunol 6:292 (1976); Hammerling et al., Monoclonal Antibodies and T Cell Hybridomas, Elsevier, N.Y. (1981)).

In particular, monoclonal antibodies can be obtained by any technique that provides for the production of antibody molecules by continuous cell lines in culture such as described in Kohler et al., Nature 256:495 (1975), and U.S. Pat. No. 4,376,110; the human B-cell hybridoma technique (Kosbor et al., Immunology Today 4:72 (1983); Cole et al., Proc Natl Acad Sci USA 80:2026 (1983)), and the EBV-hybridoma technique (Cole et al., Monoclonal Antibodies and Cancer Therapy, Alan R. Liss, Inc., pp. 77-96 (1983)). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific PSGL-1 recognition by Western blot or immunoprecipitation analysis by standard methods, for example, as described in Ausubel et al., supra. Antibodies that specifically recognize and bind to PSGL-1 are useful in the invention. Anti-PSGL-1 antibodies that bind to the PSGL-1 antigen on the surface of a T cell, e.g., a $CD3^+$ cell, and induce the depletion and/or apoptosis of T cells in an individual are particularly useful.

The antibodies can be used, for example, as part of a therapeutic regimen (e.g., to reduce or eliminate an undesirable immune response, such as a T cell mediated immune response, associated with conditions such as inflammatory diseases, autoimmune diseases, transplant rejection, allergic diseases, and T cell-derived cancers). Antibodies also can be used in a screening assay to measure the ability of a candidate compound to bind to PSGL-1.

In addition, techniques developed for the production of "chimeric antibodies" (Morrison et al., Proc Natl Acad Sci USA 81:6851 (1984); Neuberger et al., Nature 312:604 (1984); Takeda et al., Nature 314:452 (1984)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region.

Alternatively, techniques described for the production of single chain antibodies (U.S. Pat. Nos. 4,946,778, 4,946,778, and 4,704,692) can be adapted to produce single chain antibodies against a PSGL-1 polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275 (1989)) to allow rapid and easy identification of monoclonal Fab fragments with the desired specificity.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics 7:13 (1994); and U.S. Pat. Nos. 5,545,806 and 5,569,825).

Multimeric Compounds

Multimeric compounds that bind to a plurality of PSGL-1 proteins on the surface of a T cell or NK cell can be used to induce apoptosis in the cell. The multimeric compound contains at least two polypeptide chains. Each of the polypeptide chains contains (i) a binding domain that binds to PSGL-1, and (ii) a heterologous amino acid sequence.

In general, a multimeric compound binds to at least two different PSGL-1 proteins on the surface of a given cell. However, a multimeric compound can be formulated to have 3, 4, 5, 6, 7, 8, 9, 10, 11, 12, or more distinct PSGL-1 binding domains, thereby causing the multimeric compound to bind to 3, 4, 5, 6, 7, 8, 9, 10, 11, 12, or more different PSGL-1 proteins on the surface of a given cell.

A binding domain can contain any amino acid sequence (or any amino acid sequence with a modification such as, e.g., glycosylation and/or sulfation) that binds to PSGL-1. The binding domain can correspond to either a naturally occurring or a non-naturally occurring amino acid sequence. For example, a binding domain can contain the PSGL-1-binding domain of a selectin (e.g., P-selectin, E-selectin, or L-selectin). A polypeptide containing a PSGL-1 binding domain of a selectin can optionally include: (i) an extracellular domain of the selectin (e.g., P-selectin, E-selectin, or L-selectin); (ii) a calcium dependent lectin domain of the selectin (e.g., P-selectin, E-selectin, or L-selectin); or (iii) a fragment of the extracellular domain of the selectin (e.g., P-selectin, E-selectin, or L-selectin) that mediates binding to PSGL-1. In addition to these naturally occurring amino acid sequences, one or more amino acid changes can be introduced into a naturally occurring PSGL-1 binding domain, resulting in a non-naturally occurring sequence that retains PSGL-1-binding function. For example, a polypeptide can contain an amino acid sequence that binds to PSGL-1 and is at least 80%, 85%, 90%, 95%, or 98% identical to any of: (i) an extracellular domain of a selectin (e.g., P-selectin, E-selectin, or L-selectin); (ii) a calcium dependent lectin domain of a selectin (e.g., P-selectin, E-selectin, or L-selectin); or (iii) a fragment of the extracellular domain of a selectin (e.g., P-selectin, E-selectin, or L-selectin) that mediates binding to PSGL-1. Standard molecular biology mutagenesis techniques can be used to introduce changes into a nucleic acid sequence encoding a PSGL-1 binding domain. Modified binding domains can then be tested for their ability to bind to PSGL-1, e.g., immobilized PSGL-1 or PSGL-1 on the surface of a cell. A binding domain can also contain the PSGL-1 binding domain of an anti-PSGL-1 antibody or a polypeptide selected from a phage display library, or a an amino acid sequence that binds to PSGL-1 and is at least 80%, 85%, 90%, 95%, or 98% identical to the PSGL-1 binding domain of an anti-PSGL-1 antibody or a polypeptide selected from a phage display library.

A PSGL-1-binding domain can contain an amino acid sequence that corresponds to a PSGL-1-binding fragment of P-selectin. An example of a polypeptide chain (of a multimeric compound described herein) containing such an amino acid sequence is a recombinant mouse P-selectin/Fc chimera (available from R&D Systems, Minneapolis, Minn.) containing the following components: (i) CD33 signal peptide (Met1-Ala16); (ii) mouse P-selectin (Trp42-Ala709 of extracellular domain); (iii) IEGRMD (SEQ ID NO:1); and (iv) Human IgG1 (Pro100-Lys330). A second example of a polypeptide chain containing such an amino acid sequence is a recombinant human P-selectin/Fc chimera (available from R&D Systems, Minneapolis, Minn.) containing the following components: (i) human P-selectin (Met1-Ala771, extracellular domain); (ii) IEGRMD (SEQ ID NO:1); and (iii) Human IgG1 (Pro100-Lys330).

A PSGL-1-binding domain can contain an amino acid sequence that corresponds to a PSGL-1-binding fragment of E-selectin. An example of a polypeptide chain (of a multimeric compound described herein) containing such an amino acid sequence is a recombinant mouse E-selectin/Fc chimera (available from R&D Systems, Minneapolis, Minn.) containing the following components: (1) mouse E-selectin (Met1-Pro557, extracellular domain); (ii) IEGRMD (SEQ ID NO:1); (iii) Human IgG1 (Pro100-Lys330); and (iv) HHHHHH (SEQ ID NO:2). A second example of a polypeptide chain containing such an amino acid sequence is a recombinant human E-selectin/Fc chimera (available from R&D Systems, Minneapolis, Minn.) containing the following components: (i) human E-selectin (Met1-Pro556, extracellular domain); (ii) IEGRMD (SEQ ID NO:1); (iii) human IgG1 (Pro100-Lys330); and (iv) HHHHHH (SEQ ID NO:2).

A PSGL-1 binding domain can contain an amino acid sequence that corresponds to a PSGL-1-binding fragment of L-selectin. An example of a polypeptide chain (of a multimeric compound described herein) containing such an amino acid sequence is a recombinant mouse L-selectin/Fc chimera (available from R&D Systems, Minneapolis, Minn.) containing the following components: (i) mouse L-selectin (Met1-Asn332, extracellular domain); (ii) IEGRMD (SEQ ID NO:1); (iii) Human IgG1 (Pro100-Lys330); and (iv) HHHHHH (SEQ ID NO:2). A second example of a polypeptide chain containing such an amino acid sequence is a recombinant human L-selectin/Fc chimera (available from R&D Systems, Minneapolis, Minn.) containing the following components: (i) human L-selectin (Met1-Asn332, extracellular domain); (ii) IEGRMD (SEQ ID NO:1); (iii) Human IgG1 (Pro100-Lys330); and (iv) HHHHHH (SEQ ID NO:2).

A multimeric compound can be formulated as a homo-multimeric compound or a hetero-multimeric compound. A homo-multimeric compound contains only polypeptide chains that have identical PSGL-1 binding domains. For example, a homo-multimeric compound can contain polypeptide chains containing identical PSGL-1-binding fragments of P-selectin. A hetero-multimeric compound contains polypeptide chains that have different PSGL-1 binding domains. For example, a hetero-multimeric compound can contain a first polypeptide chain that contains a PSGL-1-binding fragment of P-selectin and a second polypeptide chain that contains a PSGL-1-binding fragment of E-selectin.

A heterologous amino acid sequence can be any amino acid sequence. However, the amino acid sequence of the polypeptide chains described herein does not correspond to the sequence of a naturally occurring protein. A heterologous amino acid sequence contains one or more amino acids that permit the linkage of the polypeptide chains. For example, the one or more amino acids can covalently link, e.g., via a disulfide linkage, the polypeptide chains. One example of a heterologous sequence is an immunoglobulin heavy chain constant region. Disulfide bonding between Fc regions of two polypeptide chains can result in the formation of a dimeric compound.

In addition to contributing to the linkage of the polypeptide chains, the heterologous amino acid sequence can also contain a cross-linker binding region, e.g., a cell surface receptor binding region. Upon the binding of an agent to such a binding region, cross-linking of the polypeptide chains and the cell surface PSGL-1 proteins to which they are bound can result. An immunoglobulin heavy chain constant region contains an Fc receptor binding region. A cross-linker can be, for example, an antibody (e.g., an anti-Fc antibody) that specifically binds to the cross-linker binding region of the heterologous amino acid sequence.

Screening Assays for Compounds that Modulate PSGL-1 Function

The invention also encompasses methods for identifying compounds that interact with PSGL-1 (or a domain of PSGL-1) including, but not limited to, compounds that induce T cell depletion and/or T cell apoptosis upon binding to PSGL-1. Also included are compounds that modulate the interaction of PSGL-1 with transmembrane, extracellular, or intracellular proteins that regulate PSGL-1 activity and compounds which modulate PSGL-1 activity.

The compounds that may be screened in accordance with the invention include, but are not limited to peptides, antibodies and fragments thereof, and other organic compounds that bind to PSGL-1 and modulate a biological function mediated by PSGL-1, as described herein.

Such compounds may include, but are not limited to, peptides such as, for example, soluble peptides, including but not limited to members of random peptide libraries; (Lam et al., Nature 354:82 (1991); Houghten et al., Nature 354:84 (1991)), and combinatorial chemistry-derived molecular library made of D- and/or L configuration amino acids, phosphopeptides (including, but not limited to, members of random or partially degenerate, directed phosphopeptide libraries; Songyang et al., Cell 72:767 (1993)), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

Other compounds which can be screened in accordance with the invention include but are not limited to small organic molecules that affect an activity of the PSGL-1 protein, as described herein.

Computer modeling and searching technologies permit identification of compounds, or the improvement of already identified compounds, that can modulate PSGL-1 expression or activity. Having identified such a compound or composition, the active sites or regions are identified. Such active sites might typically be a binding site for a natural modulator of activity. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the modulator (or ligand) is found.

Although described above with reference to design and generation of compounds which could alter binding, one could also screen libraries of known compounds, including natural products or synthetic chemicals, and biologically active materials, including proteins, for compounds which bind to a PSGL-1 protein and cause T cell depletion and/or induce T cell apoptosis.

In vitro systems may be designed to identify compounds capable of interacting with PSGL-1 (or a domain of PSGL-1). Compounds identified may be useful, for example, in modulating T cell activity as described herein and thus may be useful for the treatment of conditions associated with an excessive or unwanted T cell mediated immune response or excessive or unwanted T cell proliferation such as inflammation, autoimmunity, transplant rejection, an allergic condition, or a T cell cancer.

The principle of the assays used to identify compounds that bind to PSGL-1 involves preparing a reaction mixture of PSGL-1 (or a domain thereof) and the test compound under conditions and for a time sufficient to allow the two components to interact and bind, thus forming a complex which can be removed and/or detected in the reaction mixture. The PSGL-1 species used can vary depending upon the goal of the screening assay. In some situations it is preferable to employ a peptide corresponding to a domain of PSGL-1 fused to a heterologous protein or polypeptide that affords advantages in the assay system (e.g., labeling, isolation of the resulting complex, etc.) can be utilized.

The screening assays can be conducted in a variety of ways. For example, one method to conduct such an assay involves anchoring PSGL-1 protein, polypeptide, peptide or fusion protein or the test substance onto a solid phase and detecting PSGL-1/test compound complexes anchored on the solid phase at the end of the reaction. In one embodiment of such a method, the PSGL-1 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for PSGL-1 protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with PSGL-1. To this end, cell lines that express PSGL-1, or cell lines that have been genetically engineered to express PSGL-1 can be used. Cell based assays are particularly useful for evaluating the functional effects of a compound identified by a screen described herein. For example, once a compound is identified based upon its ability to bind to a PSGL-1 protein, the compound can then be tested for its ability to, e.g., induce T cell apoptosis in vitro or in vivo or deplete T cells in vitro or in vivo.

Pharmaceutical Compositions

Given that an object of the present invention is to alter an immune response in an individual, a pharmaceutical composition containing, for example, antibodies, multimeric compounds, small molecules, or other compounds that specifically bind PSGL-1 polypeptides are also a feature of the invention. In a preferred example, the compound functions as an agonist of PSGL-1.

Pharmaceutical compositions for use in accordance with the present invention can be formulated in a conventional manner using one or more physiologically acceptable carriers or excipients. Thus, the compounds and their physiologically acceptable salts and solvates may be formulated for administration by a variety of routes of administration.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form for constitution with a suitable vehicle, for example, sterile pyrogen-free water, before use.

Methods of Controlling a T Cell-Mediated Immune Response and Depleting T Cell Populations Compounds such as those detailed in the screening assays described herein may be useful, for example, in modulating a biological function mediated by a PSGL-1 polypeptide and/or for the treatment of disorders associated an excessive or unwanted immune response, e.g., a T cell-mediated immune response. These compounds include, but are not limited to peptides, antibodies and fragments thereof, and other organic compounds that bind to PSGL-1 on the surface of a T cell and induce a signal transduction pathway that results in the death of the T cell. The methods of the invention optionally include the addition of a cross-linking agent that induces the cross-linking of PSGL-1 on the surface of a cell. The compounds described herein can be used in any instance wherein the depletion or elimination of T cell activity is desired. Particularly useful conditions that can be treated with the compounds of the invention include inflammatory diseases, autoimmune diseases, transplant rejection, allergic diseases, and T cell-derived cancers.

Examples of conditions that can be treated with the anti-PSGL-1 compounds described herein include, but are not limited to, diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosus, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, graft-versus-host disease, cases of transplantation (including transplantation using allogeneic or xenogeneic tissues) such as bone marrow transplantation, liver transplantation, or the transplantation of any organ or tissue, allergies such as atopic allergy, AIDS, and T-cell neoplasms such as leukemias and/or lymphomas.

The methods of the invention can be used to deplete T cells from a cell population, either in vitro or in vivo. For example, a biological sample derived from an individual can be depleted of T cells in vitro by contacting the sample with an anti-PSGL-1 compound described herein, optionally together with a cross-linking agent. This method can be useful, e.g., by allowing for the enrichment of non-T cells in a cell population as well as by reducing or eliminating T cell activity from a cell population.

The following are examples of the practice of the invention. They are not to be construed as limiting the scope of the invention in any way.

EXAMPLES

Example 1

Preparation of an Anti-T Cell Apoptosis Inducing Protein ("TAIP") Monoclonal Antibody A TAIP-specific monoclonal antibody was generated by applying the well known cell fusion methods of Kohler and Milstein ((1976) European Journal of Immunology 6:511-519) to produce a hybridoma secreting desired antibodies. Antibody-producing cells from a hamster injected with Concanavalin A (Con A)-activated Balb/c spleen T cells were fused with a myeloma cell line to form an antibody secreting hybridoma. The two populations of cells were fused with polyethylene glycol, and the resulting antibody producing cells were cloned and propagated by standard tissue culture methods. One hybridoma generated according to these methods secreted a monoclonal antibody, designated TAB4, that was able to induce T cell apoptosis in vitro and deplete T cells in vivo. The protein recognized by TAB4 was designated T cell apoptosis inducing protein (TAIP).

C57BL/6J (B6) and BALB/c mice were purchased from the Jackson lab (Bar Harbor, Me.). Syrian hamsters were purchased from the Animal Core Facility, National Taiwan University Medical College.

Concentrated culture supernatant of the TAB4 hybridoma was spun at 20,000×g for 10 minutes and the supernatant was diluted at a 1:1 ratio with the binding buffer (0.1 M sodium acetate, pH 5.0). A protein G column (approximately 1 ml bed volume) was washed three times with 3-5 ml of the binding buffer. The cleared culture supernatant was loaded to the protein G column and the flow-through was collected and reloaded to the column. The column was washed with 6-10 ml of the binding buffer and the bound antibody was eluted from the column with 5 ml of the elution buffer (0.1 M glycine-HCl, pH 2.8). Each fraction contained 1 ml of the eluted antibody and the eluted fraction was adjusted to neutral pH by mixing each 1 ml fraction with 50 microliters of 1 M Tris-HCl, pH 7.5. Fractions containing the antibody were pooled and dialyzed against 2 liters of PBS, pH 7.4 three times at three hours for each dialysis. Protein concentration in the antibody samples were determined with the procedure described by Bradford using the Bio-Rad Protein Assay (BIO-RAD, Hercules, Calif.).

Example 2

Preparation of a Mouse Spleen Cell Suspension and the Activation and Enrichment of T cells Mouse spleen was immersed in 8 ml of Hank's balanced salt solution (HBSS), gently minced with a sterile cover slip, transferred to a 15 ml centrifuge tube (Costar), and spun at 200×g for 5 minutes. The supernatant was discarded and the cell pellet was resuspended in the residual buffer by gently tapping the wall. The contaminating red blood cells (RBC) were lysed by the addition of 1 ml of RBC lysis buffer (0.6 M $NH_4Cl$, 0.17 M Tris-base, pH 7.65), followed by a 2 min incubation at room temperature and rapid quenching with 9 ml of HBSS. The cells were pelleted at 200×g for 5 minutes, washed twice and resuspended in RPMI medium. The concentration and viability of cells in the mixture were determined with a hemocytometer (Cambridge Scientific Inc.) and Trypan blue exclusion.

The spleen cells were adjusted to a final concentration of $3 \times 10^6$/ml with RPMI medium and Concanavalin A was added to a final concentration of 2 micrograms/ml to activate the T cells. The cell suspension was transferred to a 6-well culture plate (5 ml/well) or a 10-cm culture dish (10 ml/dish) and incubated at 37° C., 5% $CO_2$ for 48 hours before harvesting. The activated spleen cells, including activated T cells, were resuspended in 5 ml of HBSS and carefully overlaid on top of a 5 ml 55% cushion of Percoll solution in a centrifuge tube. Care was taken not to disturb the separated layers. The cells were spun at 1,900×g for 13 minutes at 25° C. without the brake. The enriched T cells were collected from the interface of the two layers, washed twice with HBSS, and were ready for experiments.

Example 3

Apoptosis of Activated T cells

Activated T cells (see Example 2) were resuspended to a final concentration of $5 \times 10^5$ cells/ml in RPMI medium containing 5 ng/ml of IL-2, and treated with control Ig, TAB4, or anti-CD3 according to the conditions shown in Table 1.

TABLE 1

| Experiment groups | Treatment* |
|---|---|
| Negative control | 3 ug/ml hamster Ig |
|  | 5 ng/ml IL-2 |
|  | 3 ug/ml cross-linker antibody (anti-hamster Ig) |
| TAB4 | 3 ug/ml TAB4 hamster mAb |
|  | 5 ng/ml IL-2 |
|  | 3 ug/ml cross-linker antibody (anti-hamster Ig) |
| Positive control | 1 ug/ml anti-CD3 mAb |
|  | 5 ng/ml IL-2 |
|  | 1 ug/ml cross-linker antibody (anti-mouse Ig) |

*Final concentration of the designated reagents in the medium.

After an incubation period of 18-24 hours, the extent of apoptosis in each culture was determined using the 7-AAD apoptosis assay. The treated cells were transferred to FACS tubes (Falcon), washed twice with ice-cold FACS solution (1% fetal bovine serum, 0.05% sodium azide in PBS), pelleted at 200×g at 4° C. The cells were resuspended in ice-cold FACS solution to a final concentration of $1-2 \times 10^7$ cells/ml. For staining, 0.1 ml of the resuspended cells were mixed with 7-AAD to a final concentration of 2 ug/ml and then incubated at 4° C. in the dark for 20 minutes. Finally, the stained cells were washed twice with ice-cold FACS solution, resuspended in 0.5 ml of FACS solution and analyzed with BD™ LSR flow cytometer (Becton Dickinson).

FIG. 1 depicts the results of a representative time-course experiment that investigated when activated T cells acquire sensitivity to TAB4 (anti-TAIP)-mediated apoptotic signals. Mouse splenocytes were activated with Con-A and maintained in IL-2 containing medium. Activated T cells were harvested, resuspended, and challenged with TAB4 monoclonal antibody or control hamster IgG in the presence of anti-hamster IgG antibody as cross-linker. The ability of TAIP cross-linking to induce low level (6.5%) of apoptotic cell death was evident on day one. However, the extent of TAB4-induced apoptosis increased from 17% on day 2, peaked at 52% on day 4, and declined to 44% on day 6. The control hamster IgG did not induce specific apoptotic T cell death, as compared with the cultures that received only IL-2. Anti-CD3 (as positive control) induced apoptosis in 38% of T cell after 48 hours of activation (data not shown).

Example 4

Expression of the TAIP Antigen in Different Tissues

Cells were washed twice with ice-cold FACS solution (1% fetal bovine serum, 0.05% sodium azide in PBS) and spun at 200×g at 4° C. in a FACS tube (Falcon). The cells were resuspended in ice-cold FACS solution to a final concentration of $1 \times 10^7$ cells/ml and a 0.1 ml aliquot of the resuspended cells in a FACS tube (Falcon) was used for each assay. For surface staining, the TAB4 monoclonal antibody or a control hamster Ig at a final concentration of 2 ug/ml were added to the cells and the mixtures were incubated at 4° C. for 30 minutes in the dark. The cells were washed once with ice-cold FACS and then stained with: (1) for spleen cells, cychrome-conjugated anti-CD3 antibody (2 ug/ml), FITC-conjugated anti-hamster Ig, and PE-conjugated anti-CD8/CD4/CD19/CD11b/pan-NK/I-A/I-E/Mac-3 antibody (2 ug/ml) in 100 ul of ice-cold FACS solution; and (2) for thymus cells, FITC-conjugated anti-hamster Ig, PE-conjugated anti-CD8, and cychrome-conjugated anti-CD4 antibodies (2 ug/ml) in 100 ul of ice-cold FACS solution. The reaction was performed at 4° C. for 30 minutes in the dark. Finally, the stained cells were washed twice with ice-cold FACS solution, resuspended in 1 ml of FACS solution and analyzed with BD™ LSR flow cytometer (Becton Dickinson).

Figure 3:
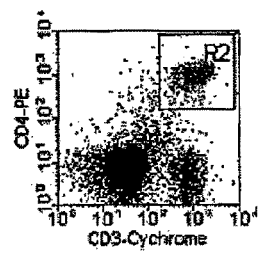
FIG. 3 depicts the expression of the PSGL-1 antigen on spleen CD4⁺ T cells, CD8⁺ T cells, CD19⁺ B cells, and NK cells.
Figure 3:
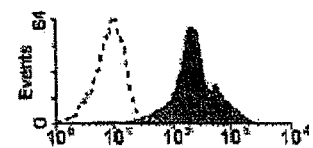
Figure 3:
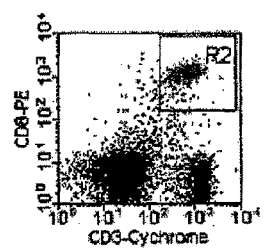
Figure 3:
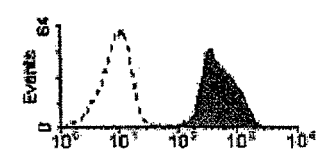
Figure 3:
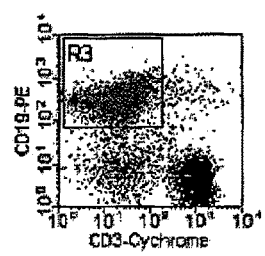
Figure 3:
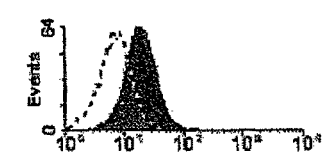
Figure 3:
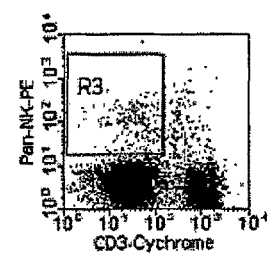
Figure 3:
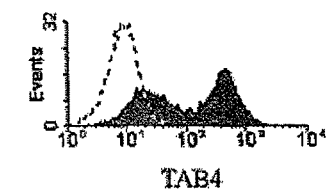
Figure 4:
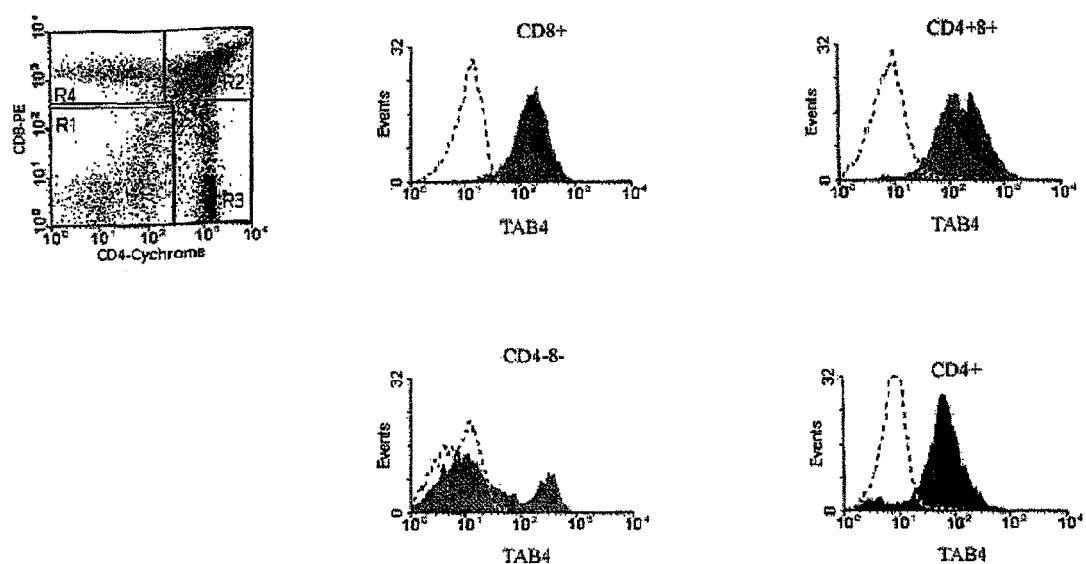
FIG. 4 depicts the expression of the PSGL-1 antigen on CD4⁺, CD8⁺, and CD4⁺8⁺, and CD4⁻8⁻ thymocytes.

FIGS. 3 and 4 demonstrate by FACS analysis the distribution of TAIP antigen on the various subpopulations of splenocytes and thymocytes. As shown in FIG. 3, $CD19^+$ B cells expressed low but detectable amounts of TAIP proteins on the surface. Significantly higher amounts of TAIP proteins were detected on $CD3^+$ T cells and a fraction of NK cells. Most of the $CD4^+$, $CD8^+$, and $CD4^+8^+$ thymus T cells expressed significant amounts of TAIP proteins. In contrast, the TAIP proteins were expressed only on a small population of $CD4^-8^-$ thymus T cells (FIG. 4).

Tissues from B6 and BALB/c mice, including brain, thymus, heart, lung, liver, stomach, kidney, spleen, and skin, were collected, fixed in 10% formaldehyde overnight at room temperature, and embedded in paraffin blocks. Tissue sections, at a 4 um thickness, were prepared from the paraffin block with Leica RM2135 microtome, spread in 45° C. water, and laid on a coated slide. The slides were dried in 37° C. and were ready for subsequent experiments.

Slides containing the tissue paraffin sections were dewaxed and dried through a xylenes-100% ethanol series according to standard protocol and were finally kept in 100% ethanol. The sections were rehydrated through a 100% ethanol-90% ethanol-85% ethanol-70% ethanol-PBS serial incubation according to standard protocol to a final PBS solution. The following reactions were all performed in a humidified box. Non-specific binding were blocked by incubating the tissue sections in blocking buffer (1% normal goat serum) for 1 hour at room temperature (or 4° C. overnight). The blocking buffer was removed and TAB4 or normal hamster Ig (1:200 dilution) was added to the sections and incubation continued for another hour at room temperature (or 4° C. overnight). The sections were washed twice in PBS, for 5 minutes each to remove the primary antibody, reacted with 1:250 diluted alkaline phosphatase-conjugated goat anti-hamster Ig, and incubated at room temperature for 1 hour. The sections were again washed twice with PBS, 5 minutes each, to remove the antibody-enzyme conjugate and the color reaction was developed with BCIP/NBT substrate solution at room temperature for 30 minutes in the dark. The sections were washed again with PBS to remove excess enzyme substrate, dehydrated through the PBS-ethanol-xylenes series, and mounted for microscopy.

The results indicated that the TAIP proteins expression were detected only in bone marrow derived-tissues but not on the rest of the tissues tested.

Example 5

Cell Surface Biotinylation and Immunoprecipitation of the TAIP Antigen $5 \times 10^7$ RL♂1 or NIH-3 T3 cells were surface biotinylated in 1 ml of PBS containing 0.5 mg/ml Sulfo-NHS-biotin (Pierce) for 30 minutes on ice. The reaction was terminated by incubating the cells with 0.5 ml of Dulbecco's modified Eagle's medium (Life Technologies, Inc.) for 10 minutes on ice. Cells were washed with 1 ml of Dulbecco's modified Eagle's medium once and with 1 ml of phosphate-buffered saline twice.

Labeled cells were lysed at a density of $5.0 \times 10^7$ cells/ml in cold lysis buffer (1% Triton X-100, 20 mM Tris-HCl, pH 8.0, 160 mM NaCl, 1 mM $CaCl_2$) containing complete protease inhibitor cocktail (Roche) for 15 minutes, and insoluble material was pelleted at 10,000×g for 10 minutes; these and all subsequent steps were performed at 4° C. For immunoprecipitation, the lysate was preincubated for 30 minutes with 50 µl of packed protein G-Sepharose (Amersham Pharmacia Biotech) to remove non-specifically binding proteins. Beads were pelleted, and aliquots of the supernatant (routinely corresponding to $5.0 \times 10^7$ cells) were incubated with 20 µl of protein G-Sepharose preloaded with 10 µg of mAb TAB4 or IgG from normal hamster serum. After m incubation for 4 h at 4° C., the resin was washed four times with washing buffer (0.05% Triton X-100, 50 mM Tris-HCl, pH 8.5, 400 mM NaCl, 1 mM $CaCl_2$, 1 mg/ml ovalbumin), twice with a similar washing buffer, containing 250 mM instead of 400 mM NaCl. Proteins specifically bound to the TAB4 were eluted with 50 µl of 1×SDS sample buffer. Eluted proteins were separated by 8% SDS-PAGE and transferred to nitrocellulose membrane (Millipore). Filters were analyzed for biotinylated proteins with peroxidase-conjugated Avidin (PharMingen) and developed with the Chemiluminescence reagent (NEN™ Life Science Products).

Figure 2:
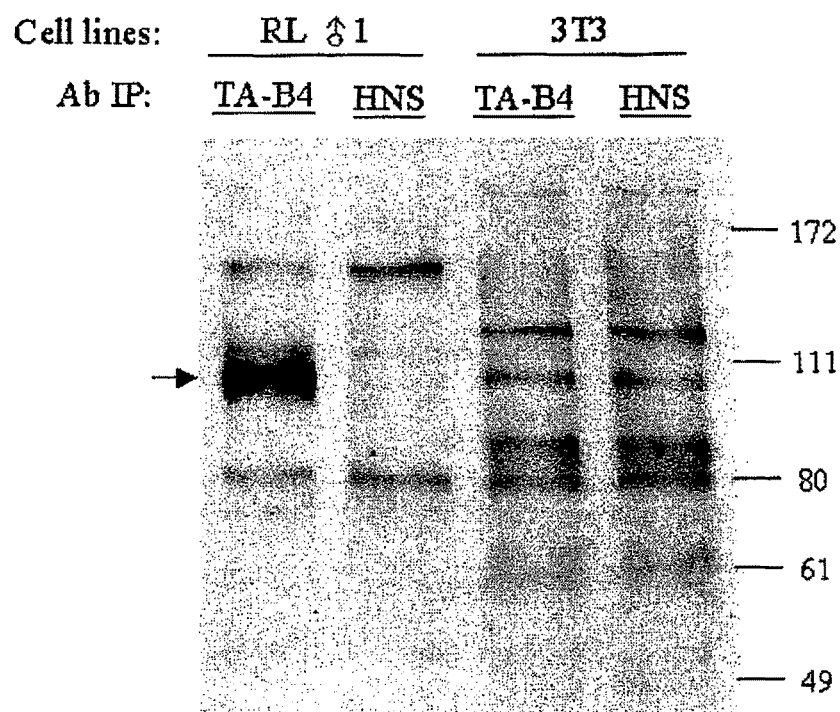
FIG. 2 depicts the results of cell surface biotinylation and immunoprecipitation of the antigen recognized by the TAB4 antibody.

As shown in FIG. 2, a biotinylated surface protein with a molecular weight of approximately 120-kD was identified by TAB4 in RL♂1 cells (TAIP⁺ T cells), but not in 3T3 cells (TAIP⁻ cells). In contrast, protein G sepharose coated with hamster normal serum could not retrieve this 120-kDa protein. These results suggest that this 120-kDa protein is the antigen recognized by monoclonal antibody TAB4 on the cell surface of T cells.

Example 6

Depletion of T Cells In Vivo

To examine the effects of TAB4 on populations of T cells and other cells in vivo, mice were injected with 300 ug of TAB4 or control hamster Ig intraperitoneally and, on day 4, splenocytes, thymocytes, and peripheral blood mononuclear cells were harvested for the total cell count and for the analyses of cell surface markers by FACS.

For FACS assays, the cells were fixed with 2% paraformaldehyde at 4° C. for 20 minutes, washed twice, and resuspended in ice-cold FACS solution to a final concentration of $1 \times 10^7$ cells/ml. A 100 ul aliquot of the resuspended cells in a FACS tube (Falcon) was used for each assay. TAB4 or control hamster Ig at a final concentration of 2 ug/ml were added to the cells and the mixtures were incubated at 4° C. for 30 minutes in the dark. The cells were washed once with ice-cold FACS and reacted with: (1) for spleen cells, cychrome-conjugated anti-CD3 antibody (2 ug/ml), FITC-conjugated anti-hamster Ig and PE-conjugated anti-CD8/CD4/CD19/CD11b/pan-NK/I-A/I-E/Mac-3 antibody (2 ug/ml) in 100 ul of ice-cold FACS solution; and (2) for thymus cells, FITC-conjugated anti-hamster Ig, PE-conjugated anti-CD8, and cychrome-conjugated anti-CD4 antibodies (2 ug/ml) in 100 ul of ice-cold FACS solution. The reaction was performed at 4° C. for 30 minutes in the dark. Finally, the stained cells were washed twice with ice-cold FACS solution, resuspended in 1,000 ul of FACS solution and analyzed with BD™ LSR flow cytometer (Becton Dickinson).

TABLE 2

| $\times 10^6$ | No Treatment | Normal Hamster Ig | TAB4-treated | Depletion (%) |
|---|---|---|---|---|
| Spleen | | | | |
| Total Splenocytes | 123 | 93.3 | 105 | 14.6 |
| CD3⁺ T cells | 32.8 | 28.4 | 12.4 | 62.2 |
| CD3⁻ CD19⁺ | 72.2 | 53.4 | 72.9 | −0.8 |
| CD3⁻ NK⁺ | 3.6 | 2.4 | 1.80 | 50 |
| Peripheral Blood Leukocytes | | | | |
| CD3⁺ T cells | 36.7% | 36% | 4.1% | 88.8% |
| Thymus | | | | |
| Total Thymocytes | 94 | 229 | 45 | 52.1 |
| CD4⁺ | 9.3 | 28.4 | 10.9 | −16.6 |
| CD8⁺ | 5.2 | 7.7 | 3.6 | 30.3 |
| CD4⁺ CD8⁺ | 73.8 | 182 | 26 | 64.7 |
| CD4⁻ CD8⁻ | 5.6 | 10.5 | 4.5 | 19.3 |

(representative data from three experiments)

Four days after the injection, the percentages of CD3⁺ T cells in peripheral blood leukocytes (PBL) decreased from 36.7% in control mice to 4.1% in TAB4-treated mice (Table 2). TAB4 treatment caused a slight reduction in the total number of splenocytes. However, in TAB4 treated mice, there was a 62% decrease in the number of CD3⁺ T cells, a 50% decrease in the number of NK cells, and a slightly increase in the total number of CD19+ B cells. The total number of thymocytes recovered from TAB4 treated mice was only 48% of the level seen in control (52% reduced). Moreover, except for CD4+ T cells, all other CD8+, CD4+CD8+, and CD4+ CD8+ T cells were reduced, with CD4+CD8+ subpopulation being the most profoundly affected (64.7% reduction).

Example 7

Anti-TAIP Antibody does not Induce IL-2 or TNF-Alpha Secretion

Figure 5:
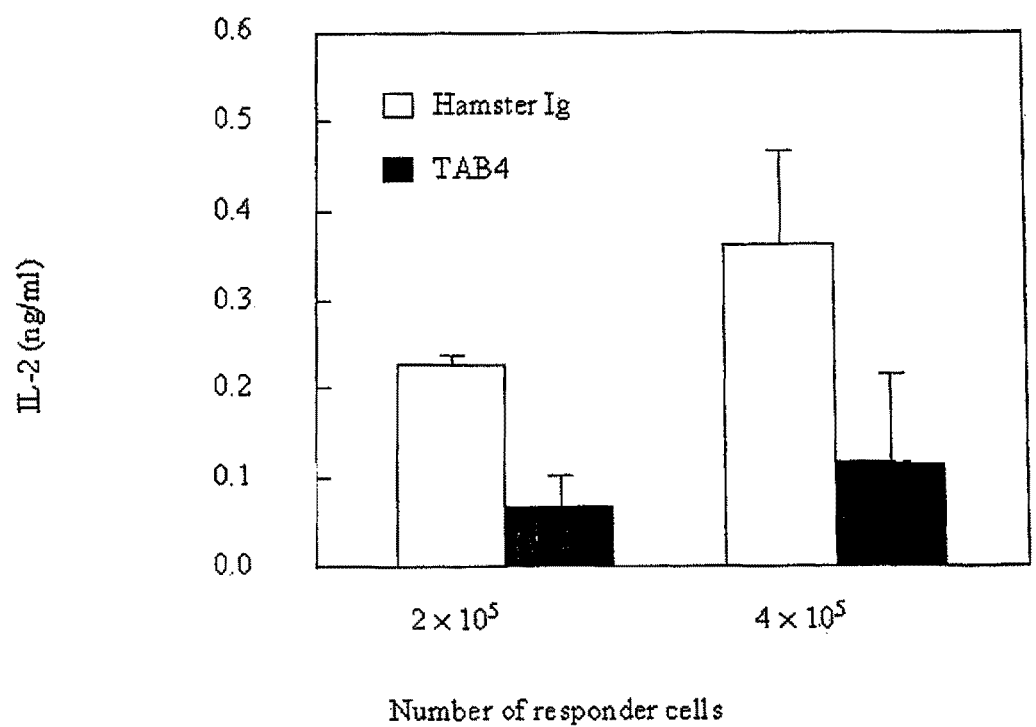
FIG. 5 depicts the levels of IL-2 produced in mixed lymphocyte culture using spleen cells isolated from TAB4 (or hamster Ig)-treated Balb/c mice as the responders and H2-mismatched C3H spleen cells as the stimulator.

Balb/c mice (H-$2^d$) were intraperitoneally injected with 300 micrograms of TAB4 or control hamster Ig. Splenocytes were isolated 7 days after injection, and used as responders in culture with mitomycin C-treated C3H(H-$2^k$) splenocytes (as stimulators). Three days later, the culture supernatants were harvested and the IL-2 content was measured by ELISA set (PharMingen). As shown in FIG. 5, the IL-2 production was suppressed in responder cells derived from TAB4-treated mice as compared with that of control mice. The plasma levels of IL-2 and TNF-alpha were also analyzed and no significant difference was noted in the levels of IL-2 (or TNF-alpha) in the sera of the control and the TAB4 treated mice. Since production of IL-2 is central to the activity of T cells, the results show that a TARP-specific antibody, such as TAB4, can be used in vivo to manipulate T cells and control unwanted T cell-mediated immune responses such as those associated with autoimmune diseases and transplantation rejection.

Example 8

Use of an Anti-TAIP Antibody to Prevent Transplant Rejection

Figure 7:
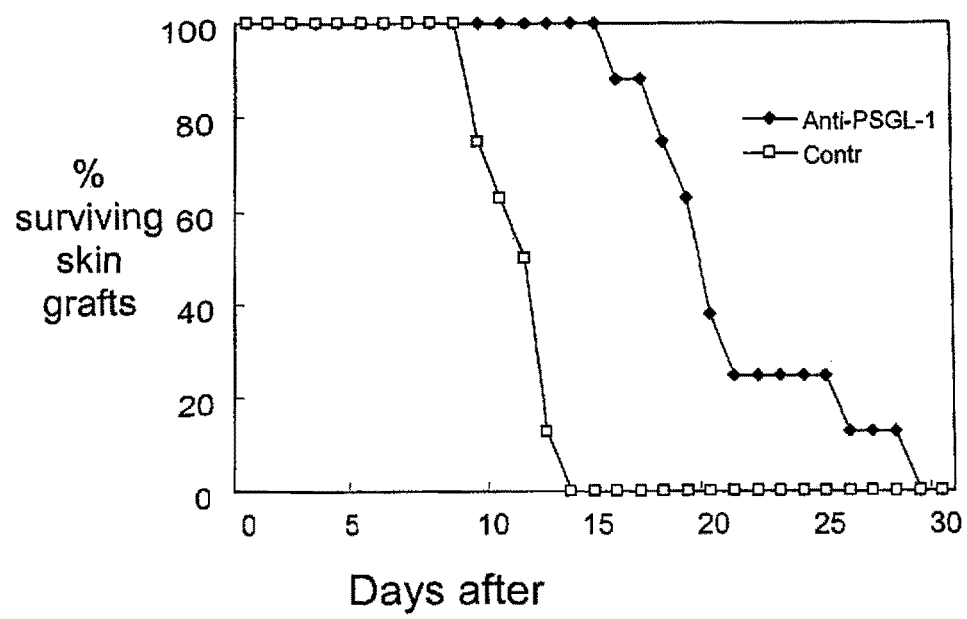
FIG. 7 depicts the percentage of surviving grafts in C57BL/6 mice that received a skin graft from Balb/c mice and were treated with an anti-PSGL-1 antibody (closed diamond) or a control antibody (open square).

Mice (obtained from Jackson Laboratory) at 8 to 12 weeks of age were anesthetized with Acepromazin maleate (Fermenta Animal Health Co., Kansas City, Mo.). Prior to skin grafting, non-thymectomized recipient C57BL/6 mice (H-$2^b$) were injected intraperitoneally with 500 ug of TAB4 or isotype control antibodies seven days before skin transplant surgery. Seven days later, a lateral flank of skin from fully allogeneic mismatched Balb/cj mice (H-$2^d$) was grafted on the lateral flank of the antibody pre-treated C57BL/6 mice. Seven days post transplantation, the mice were again injected with 500 ug of TAB4 or isotype control antibody. The mice were monitored every day after graft transplantation. The grafts were considered rejected when 50% donor skin was necrotic. The percent of graft survival is shown in FIG. 7 (n=8). The data show that TAB4 antibody treatments prolonged the survival of the allogeneic skin grafts.

Example 9

Identification of TAIP as PSGL-1

P-selectin glycoprotein ligand-1 (PSGL-1), also named CD162, is the main P-selectin ligand expressed on leukocytes, including T cells (Sako et al. (1993) Cell 75:1179; Vachino et al. (1995) J. Biol. Chem. 270:21966; Veldman et al. (1995) J. Biol. Chem. 270:16470). Biochemical characteristics of TAIP, such as its molecular weight and its tendency for dimerization suggested the possibility that TAIP may be analogous to PSGL-1. To investigate the relationship between these two antigens, the following were tested: 1) whether the antigen precipitated by TAB4 can be recognized by a commercially-available anti-PSGL-1 antibody; and 2) whether an anti-PSGL-1 antibody can deplete TAIP from the cell lysate.

RL♂1 T cells were lysed at a density of $1.0 \times 10^8$ cells/ml in lysis buffer (1% Triton X-100, mM Tris-HCl, pH 8.0, 160 mM NaCl, 1 mM $CaCl_2$) containing complete protease inhibitor cocktail for 1 hour, and insoluble material was pelleted at 10,000×g for 10 minutes. These and all subsequent steps were performed at 4° C. The lysate corresponding to $5.0 \times 10^7$ cells was incubated with 20 ul of protein G-Sepharose preloaded with 10 ug of anti-PSGL-1 mAb (clone 2PH1, PharMingen, San Diego, Calif.), anti-TAIP mAb, TAB4, or IgG from normal hamster serum. After incubation for 4 hours at 4° C., the beads were washed five times with washing buffer (0.05% Triton X-100, 50 mM Tris-HCl, pH 8.5, 400 mM NaCl, 1 mM $CaCl_2$, 1 mg/ml ovalbumin), and twice with a similar washing buffer, containing 250 mM instead of 400 mM NaCl. Bound proteins were eluted with 40 ul of 1×SDS sample buffer. Eluted proteins were separated by 6% SDS-PAGE and transferred to a nitrocellulose membrane. The membranes were immunoblotted with anti-PSGL-1 mAb, and revealed by peroxidase-conjugated goat anti-rat IgG (H+L) followed by chemiluminescence (Renaissance™, NEN).

Figure 6:
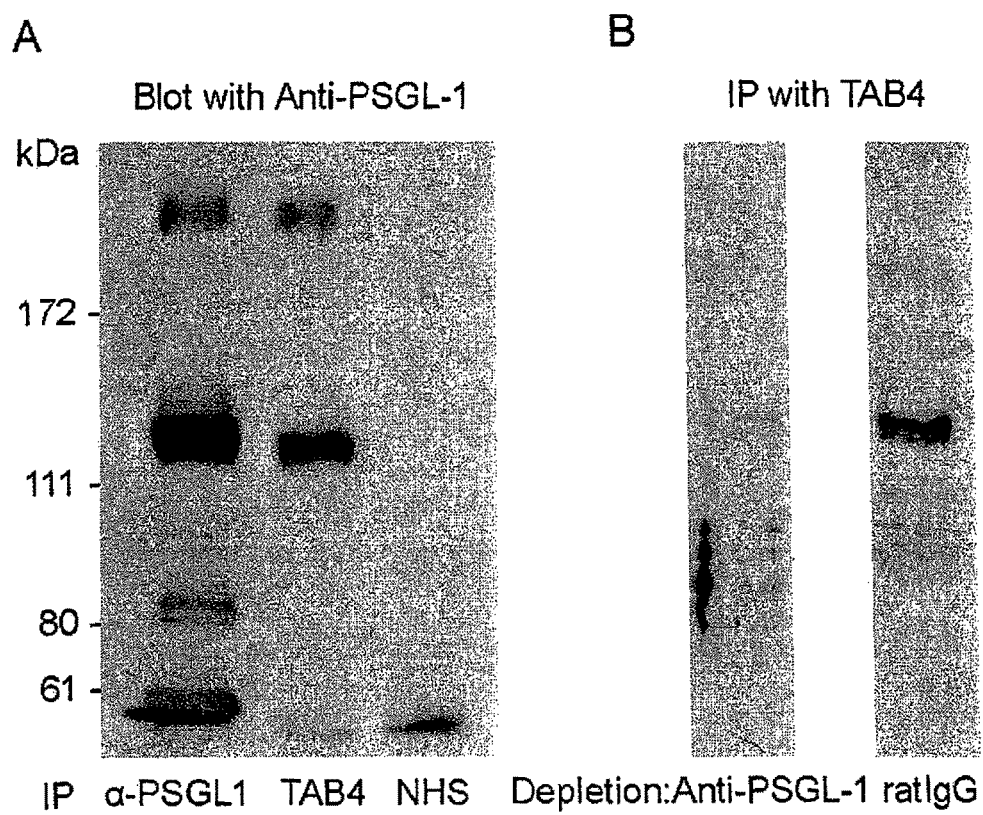
FIG. 6 depicts western blot analyses demonstrating that (A) proteins immunoprecipitated with the TAB4 antibody can be recognized by a commercially available anti-PSGL-1 antibody and (B) preclearing of T cell lysate with anti-PSGL-1 antibody can deplete the proteins recognized by the TAB4.

Surface biotinylated RL♂1 T cells were lysed at a density of $1.0 \times 10^8$ cells/ml in lysis buffer. The cell extract was incubated with 20 ug of antibody bound to 40 ul of protein G-Sepharose at 4° C. overnight. Depletions were done with anti-PSGL-1 mAb (2PH1) or control rat IgG, with TAB4 or control normal hamster serum. Depleted lysates were further subjected to do immunoprecipitation with TAB4 or anti-PSGL-1 mAb, respectively. Immunoprecipitates were separated on 6% SDS-polyacrylamide gel and detected by fluorography. As shown in FIG. 6, anti-PSGL-1 antibody can deplete TAIP protein from T cell lysates. In addition, proteins immunoprecipitated with anti-TAIP antibody (TAB4) can be recognized by anti-PSGL-1 antibody by western analysis.

Example 10

Induction of Apoptosis in Human T Cells by an Anti-PSGL-1 Antibody

To determine the role played by PSGL-1 in the apoptosis of human T cells, time-course experiments were carried out to investigate when activated human T cells acquire sensitivity toward PSGL-1-mediated apoptotic signals. Human T cells were stimulated with phytohemagglutinin (PHA) mitogen and further expanded in IL-2-containing medium. Activated T cells were harvested and then challenged with anti-PSGL-1 in the presence of IL-2 and cross-linking antibodies.

Human peripheral blood was taken from healthy adults, heparinized, and enriched for peripheral blood mononuclear cells (PBMC) based on differential density using Ficoll-Paque® PLUS (Pharmacia Biotech). The PBMC were activated with 1% PHA (Life Technologies, GibcoBRL) for 48 hours and subsequently maintained in recombinant human IL-2 (5 ng/ml) through the assay period. To assess the apoptosis-inducing ability an anti-human PSGL-1 antibody, the activated cells were treated with: (1) 1 ug/ml of the anti-PSGL-1 antibody clone KPL-1 (BD PharMingen) plus cross-linker rabbit anti-mouse Ig (0.5 ug/ml) (Jackson ImmunoResearch Laboratories); (2) isotype control purified mouse Ig plus cross-linker rabbit anti-mouse Ig; or (3) cross-linker rabbit anti-mouse Ig alone. After six hours of treatment, the percentage of early apoptotic cells was determined by FACS, staining with anti-Annexin V (BD PharMingen) and PI (Sigma).

Figure 8:
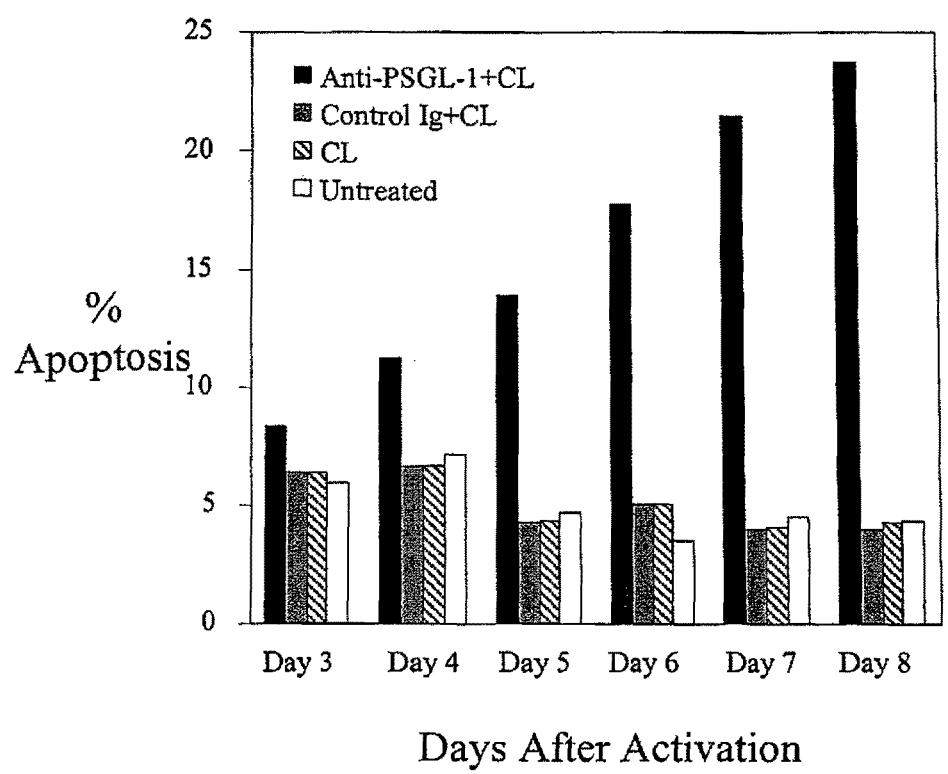
FIG. 8 depicts the time course of the percentage of apoptotic T cells following the treatment of activated human peripheral blood mononuclear cells with an anti-human PSGL-1 antibody.

As shown in FIG. 8, signaling triggered by PSGL-1 using an anti-PSGL-1 antibody plus the crosslinker triggered significant level of apoptosis in PHA-activated human PBMC (mainly T cells). The percentage of apoptotic cells increased from 8.5% on days 3 to 24% on day 8 in anti-PSGL1 treated cultures. Neither isotype-matched control, nor the cross-linking antibodies alone, had any effect on these cells.

Example 11

Use of Anti-PSGL-1 Agonist Antibody to Treat Autoimmune Disease

Non-obese diabetic (NOD) mice, a well-accepted autoimmune diabetes animal, were bred under standard conditions. Spontaneous diabetes developed in the NOD mice at the age of about 20 weeks. In the experimental group, the mice received three doses of anti-PSGL-1 antibody (TAB4) intraperitoneally at 300 μper mouse at age of 14, 15 and 17 weeks. Two additional injections with the same dose were given at the ages of 24 and 26 weeks. The control group was given hamster Ig at the same dose. Mice were monitored for glucosuria by Medi-Test Glucose strips (Macherey-Nagel, Germany) twice every week after the age of 15 weeks. Non-fasting urine glucose levels over 300 mg/dl for two consecutive measurements were considered diabetic.

Figure 9:
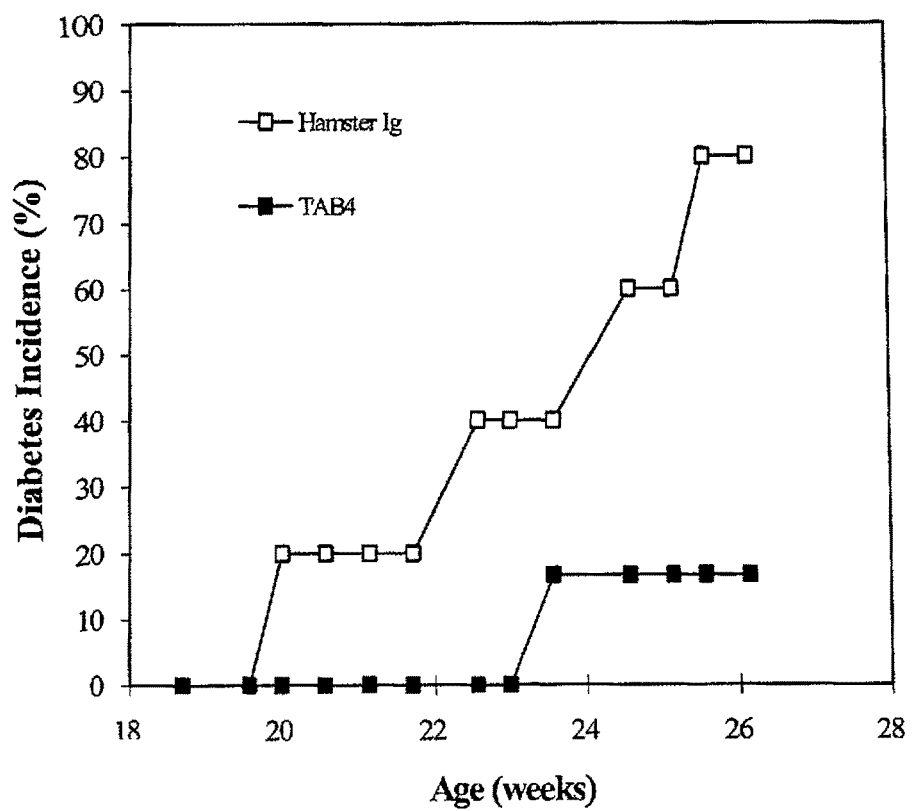
FIG. 9 depicts the incidence of diabetes in autoimmune non-obese diabetic (NOD) male mice that were treated with anti-PSGL-1 antibody (closed square) or a control antibody (open square).

As shown in FIG. 9, TAB4 (anti-PSGL-1) antibody treatment yielded significant protection as compared with control antibody treatment. Thus an anti-PSGL-1 antibody treatment can dampen the activity of autoimmune T cells and delay the onset of type I-diabetes.

Example 12

Binding of P-Seleetin, E-Selectin, and L-Selectin to Activated T Cells

To determine ability of selectins (P-Selectin, E-Selectin, and L-Selectin) to bind to activated T cells, freshly prepared splenocytes from C57BL/6 mice were activated and harvested at days 2, 4, and 6. Non-activated T cells (i.e., freshly prepared splenocytes at day 0) were also analyzed. The day 2 sample constituted $3 \times 10^6$ cells/ml of splenocytes that were activated with 2 ug/ml of Concanavalin A (Con A) in DMEM+10% FBS for 2 days. Live cells were isolated by Ficoll gradient separation. The day 4 sample was obtained from cells that were activated with Con A for 3 days and maintained in medium containing 5 ng/ml of IL-2 for an additional day. The day 6 sample was derived from cells that were activated with Con A for 3 days and maintained in 5 ng/ml of IL-2 for 3 days.

To assay the samples by FACS analysis, $2 \times 10^5$ cells per well from days 0, 2, 4 and 6 were incubated at 4° C. for 30 minutes with 40 ul/well of mouse P-Selectin, E-Selectin, or L-Selectin fused to the Fc region of human IgG1 (R&D Systems, Minneapolis, Minn.) at concentrations ranging from 20 ug/ml with two-fold serial dilution to 0.156 ug/ml. Following the incubation, cells were washed with 1×FACScan buffer (1×PBS without calcium and magnesium ions from Biochrom AG, Berlin and 2% FBS). Samples were further incubated at 4° C. for 30 minutes with 95 ul/well of anti-Thy1.2 and a secondary reagent (FITC-anti human IgG, which is specific to Fc fragment, purchased from Jackson ImmunoResearch Laboratories, Inc., West Grove, Pa.) at 3.25 ug/ml, and then washed with 1×FACScan buffer.

Figure 10:
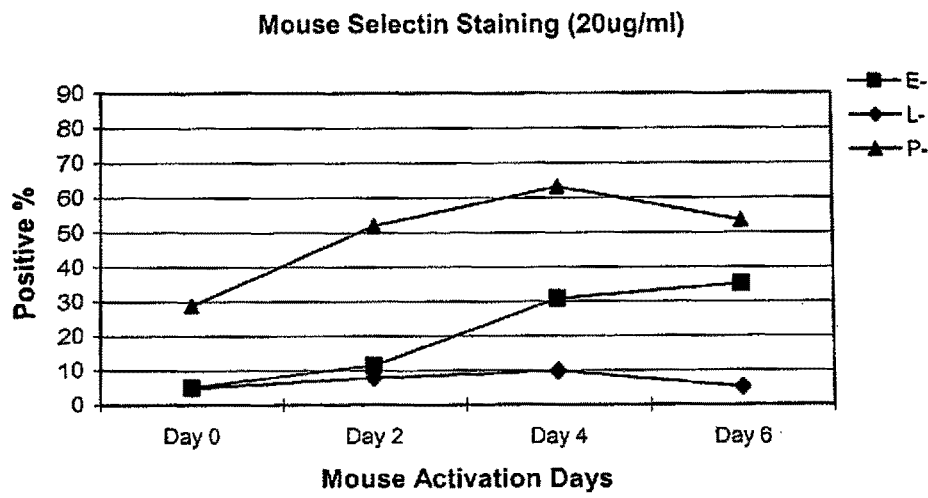
FIG. 10 depicts the binding of mouse P-selectin, E-selectin, and L-selectin to mouse activated T cells.

The results of FACSCalibur analysis are shown in FIG. 10. At 20 ug/ml, binding of P-selectin to mouse activated T cells increased gradually, peaked on day 4, and declined slightly on day 6. Binding of E-selectin rose significantly from day 2 to day 4 and then remained peaked at day 6. Binding of L-selectin to mouse activated T cells was not apparent, and did not change through the activation period, i.e. from day 0 to day 6. The results observed with L-Selectin could be due to the apparent low binding affinity of L-selectin to its ligand. Similar results were also obtained when lower concentrations of the three selectins were employed in the experiments.

Example 13

Multimeric Forms of E-Selectin and P-Selectin Induce Apoptosis of Activated T Cells A 96-well plate (NUNC™) was coated with 50 ul of anti-human Fc Ig at 20 ug/ml in 1×PBS at 4° C. overnight, blocked with 1% BSA at 37° C. for 2 hours and incubated with 50 ul of a selectin-human Fc fusion (from 0.063 to 5 ug/ml) at room temperature for 2 hours. In all experimental steps, each well was thoroughly washed five times with 1×PBS. Then $2 \times 10^5$ T cells activated previously with Con A for four days were added into each well and incubated at 37° C. for 5 hours prior to centrifugation of the plate at 200×g for 5 minutes at 4° C. The resulting pellet containing activated T cells was incubated with Annexin V-biotin conjugate at room temperature for 15 minutes and subsequently with an avidin conjugate (SA-beta-gal at 1:5000 dilution) for another 30 minutes at 37° C. In every binding reaction, each well was washed thrice with Annexin V binding buffer. The color development was achieved by incubating both 110 ul of Z-buffer mixture (54 ul of 2-mercaptoethanol in 20 ml of Z-buffer) and 30 ul of ONPG (0.04 g/10 ml) at 4° C. overnight. The readings of optical density at 420 nm were recorded.

Figure 11A:
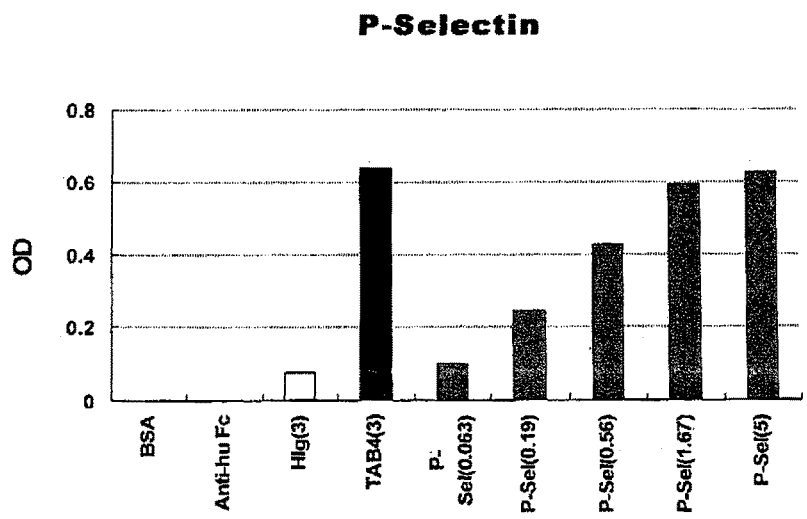
FIGS. 11A-11C depict the induction of apoptosis of mouse activated T cells by multimeric forms of E-selectin (FIG. 11A), P-selectin (FIG. 11B), and L-selectin (FIG. 1C).
Figure 11B:
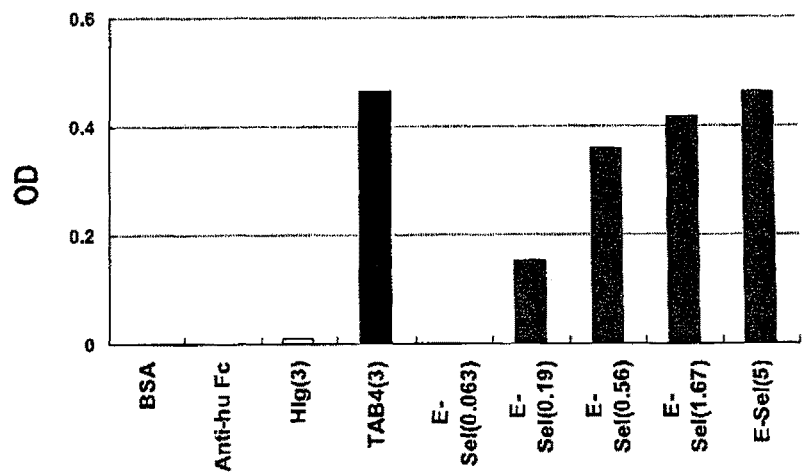
Figure 11C:
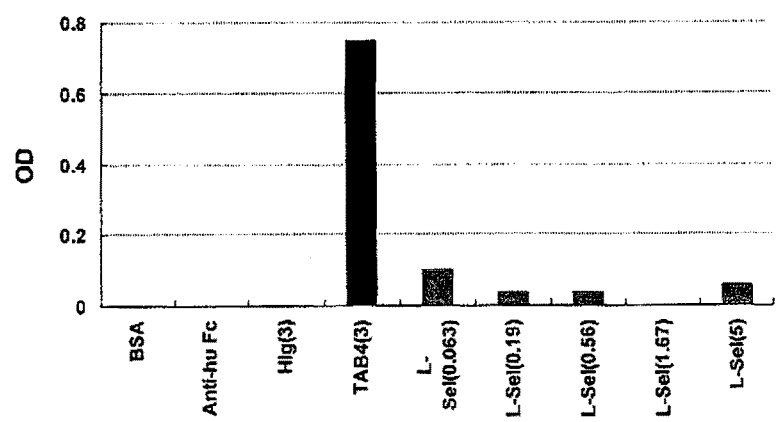

Levels of selectin-induced apoptosis of Con-A activated T cells increased with the increasing concentrations (from 0.063 ug/ml to 5 ug/ml) of P-selectin (FIG. 11A) or E-selectin (FIG. 11B) fused with Fc of human IgG1. The hamster antibody TAB4 induces apoptosis of activated T cells (see Example 1) and was used as a positive control in these experiments. As negative controls, anti-human Fc, human Ig (HIg), and BSA did not induce apoptosis. No significant apoptosis was detected in the presence of the L-selectin human Fc fusion protein (FIG. 11C), consistent with the failure of L-selectin to bind well to activated T cells (Example 12).

In summary, a plate-bound fusion protein containing a PSGL-1-binding fragment of P-selectin or E-selectin and human Fc fragment induced apoptosis of activated T cells.

Example 14

Figure 12:
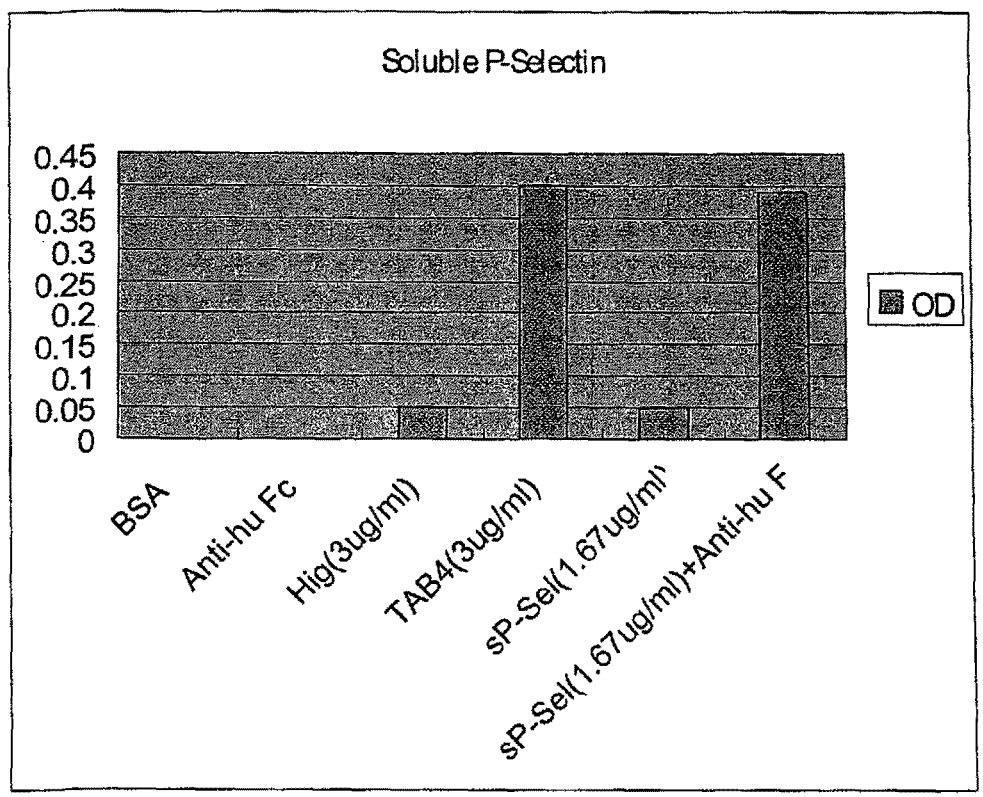
FIG. 12 depicts the induction of apoptosis of mouse activated T cells in vitro by the cross-linking of a soluble P-selectin-Fc fusion protein.

Cross-Linking of Soluble P-Selectin-Fc Fusion Protein Induces Apoptosis of Activated T Cells Mouse selectins (P-Selectin, E-Selectin, and L-Selectin) were fused to the Fc region of human IgG1 as detailed above to form soluble dimeric fusion proteins. To evaluate whether the soluble selectins can induce apoptosis of activated T cells, an experiment was performed as detailed in Example 13, with the exception that the plate-bound anti-human Fc Ig was omitted. Negligible or low levels of apoptosis of activated T cells occurred in the presence of the soluble form of P-selectin fusion protein (a dimer) alone (FIG. 12). However, upon the addition of a cross-linker (anti-human Fc) the apoptotic activity increased substantially, to approximately the apoptotic level induced in the presence of the plate-bound antibody. Neither anti-human Fc, human Ig (HIg), nor BSA induced apoptosis.

Similar results were obtained for the E-selectin-Fc fusion protein as were obtained for the P-selectin-Fc fusion protein. In addition, consistent with the results obtained for the plate-bound (multimeric form) of L-selectin, the soluble form of L-selectin fusion protein did not induce apoptosis of activated T cells.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method of delaying the onset of or reducing a T cell-mediated immune response in an individual, the method comprising: selecting an individual diagnosed as having or as being at risk of acquiring a condition characterized by an excessive or unwanted T cell-mediated immune response; and administering to the individual an anti-Fc antibody, and a multimeric compound that binds to at least two P-Selectin Glycoprotein Ligand 1 (PSGL-1) proteins on the surface of a T cell, wherein the multimeric compound comprises two polypeptide chains, each of the polypeptide chains comprising (i) a binding domain that binds to PSGL-1, wherein the binding domain comprises a P-Selectin extracellular domain or a PSGL-1-binding fragment thereof; or wherein the binding domain comprises an E-Selectin extracellular domain or a PSGL-1-binding fragment thereof, and (ii) a heterologous amino acid sequence, wherein the heterologous amino acid sequence comprises an immunoglobulin heavy chain constant region, and wherein the polypeptide chains are linked via the heterologous amino acid sequence to form the multimeric compound, wherein the binding of the multimeric compound to the at least two PSGL-1 proteins on the surface of the T cell induces a signal transduction pathway that results in the death of the T cell, thereby delaying the onset of or reducing a T cell-mediated immune response in the individual.

2. The method of claim 1, wherein the multimeric compound is a homo-multimeric compound.

3. The method of claim 1, wherein the multimeric compound is a hetero-multimeric compound.

4. The method of claim 1, wherein the polypeptide chains are covalently linked via the heterologous amino acid sequence to form the multimeric compound.

5. The method of claim 4, wherein the covalent linkage is a disulfide linkage.

6. The method of claim 1, comprising selecting an individual diagnosed as having an inflammatory disease.

7. The method of claim 1, comprising selecting an individual diagnosed as having an autoimmune disease.

8. The method of claim 1, comprising selecting an individual that has received or is expected to receive an allogeneic or xenogeneic transplant.

9. The method of claim 1, comprising selecting an individual diagnosed as having an allergic disease.

10. The method of claim 1, comprising selecting an individual diagnosed as having a T cell cancer.

11. The method of claim 1, wherein the T cell is an activated T cell.

12. The method of claim 1, wherein the method comprises determining the percentage of apoptosis of T cells in a first biological sample taken from the individual before the administration of the multimeric compound and comparing to the percentage of apoptosis of T cells in a second biological sample taken from the individual after the administration of the multimeric compound.

13. The method of claim 1, wherein the administration results in the depletion of at least 10% of activated T cells in the individual.

14. A method of inducing the death of a T cell or a natural killer (NK) cell, the method comprising: providing a T cell or NK cell expressing PSGL-1 on its cell surface; and contacting the T cell or NK cell with an anti-Fc antibody, and a multimeric compound that binds to at least two PSGL-1 proteins on the surface of the T cell or NK cell, wherein the multimeric compound comprises two polypeptide chains, each of the polypeptide chains comprising (i) a binding domain that binds to PSGL-1, wherein the binding domain comprises a P-Selectin extracellular domain or a PSGL-1-binding fragment thereof; or wherein the binding domain comprises an E-Selectin extracellular domain or a PSGL-1-binding fragment thereof, and (ii) a heterologous amino acid sequence, wherein the heterologous amino acid sequence comprises an immunoglobulin heavy chain constant region, and wherein the polypeptide chains are linked via the heterologous amino acid sequence to form the multimeric compound, wherein the binding of the multimeric compound to the at least two PSGL-1 proteins on the surface of the T cell or NK cell induces a signal transduction pathway that results in the death of the T cell or NK cell.

15. The method of claim 14, wherein the multimeric compound is a homo-multimeric compound.

16. The method of claim 14, wherein the multimeric compound is a hetero-multimeric compound.

17. The method of claim 14, wherein the polypeptide chains are covalently linked via the heterologous amino acid sequence to form the multimeric compound.

18. The method of claim 17, wherein the covalent linkage is a disulfide linkage.

19. The method of claim 14, comprising inducing the death of an activated T cell.

20. The method of claim 14, wherein the method comprises determining the percentage of apoptosis of the T cell or NK cell after the contacting with the multimeric compound.

* * * * *